United States Patent
Sato et al.

(10) Patent No.: US 10,083,562 B2
(45) Date of Patent: Sep. 25, 2018

(54) PAPER SHEET RECOGNITION APPARATUS AND PAPER SHEET RECOGNITION METHOD

(71) Applicant: GLORY LTD., Himeji-shi, Hyogo (JP)

(72) Inventors: Takeshi Sato, Hyogo (JP); Kadotaro Nishimori, Hyogo (JP); Daiki Takehara, Hyogo (JP); Hiroshi Konishi, Hyogo (JP)

(73) Assignee: GLORY LTD., Himeji-shi, Hyogo (JP)

( * ) Notice: Subject to any disclaimer, the term of this patent is extended or adjusted under 35 U.S.C. 154(b) by 0 days.

(21) Appl. No.: 15/516,392

(22) PCT Filed: Oct. 5, 2015

(86) PCT No.: PCT/JP2015/078223
§ 371 (c)(1),
(2) Date: Apr. 1, 2017

(87) PCT Pub. No.: WO2016/052749
PCT Pub. Date: Apr. 7, 2016

(65) Prior Publication Data
US 2017/0309107 A1    Oct. 26, 2017

(30) Foreign Application Priority Data
Oct. 3, 2014 (JP) .................................. 2014-205152

(51) Int. Cl.
*G07D 7/06* (2006.01)
*G07D 7/121* (2016.01)
(Continued)

(52) U.S. Cl.
CPC .............. *G07D 7/121* (2013.01); *G07D 7/12* (2013.01); *G07D 7/1205* (2017.05); *G07D 7/20* (2013.01)

(58) Field of Classification Search
CPC ........ G01N 21/27; G01N 21/55; G01N 21/59; G01N 21/64; G07D 7/12; G07D 11/0036
See application file for complete search history.

(56) References Cited

U.S. PATENT DOCUMENTS

| 4,587,434 A | * | 5/1986 | Roes | ........................ | G07D 7/162 |
|  |  |  |  |  | 250/556 |
| 5,304,813 A | * | 4/1994 | De Man | .................. | G07D 7/121 |
|  |  |  |  |  | 250/226 |

(Continued)

FOREIGN PATENT DOCUMENTS

| EP | 2 549 445 A1 | 1/2013 |
| JP | 2006-275578 A | 10/2006 |
| JP | 2009-181403 A | 8/2009 |

*Primary Examiner* — Mark J Beauchaine
(74) *Attorney, Agent, or Firm* — Renner, Kenner, Greive, Bobak, Taylor & Weber

(57) ABSTRACT

A paper sheet recognition apparatus (1) that recognizes a paper sheet based on an optical spectrum acquired from the paper sheet includes, a light source unit (31) including light sources arranged corresponding to partial areas on the paper sheet, a reading unit (32) having a light receiving surface to receive reflected lights from the partial areas, a sensor unit (34) that acquires an optical spectrum of light received by the light receiving surface, a memory (80) that stores an optical spectrum measurement condition, and a light-source control unit (72) that controls the light source unit (31) based on the optical spectrum measurement condition. The optical spectrum measurement condition includes information for identifying at least one light source corresponding to the predetermined partial area, information for identifying a timing for turning on the identified light source, and information for identifying a timing for turning off the light source.

10 Claims, 21 Drawing Sheets

(51) Int. Cl.
*G07D 7/1205* (2016.01)
*G07D 7/20* (2016.01)
*G07D 7/12* (2016.01)

(56) References Cited

U.S. PATENT DOCUMENTS

2014/0218734 A1 8/2014 Shimaoka et al.
2015/0249104 A1 9/2015 Ota et al.

* cited by examiner

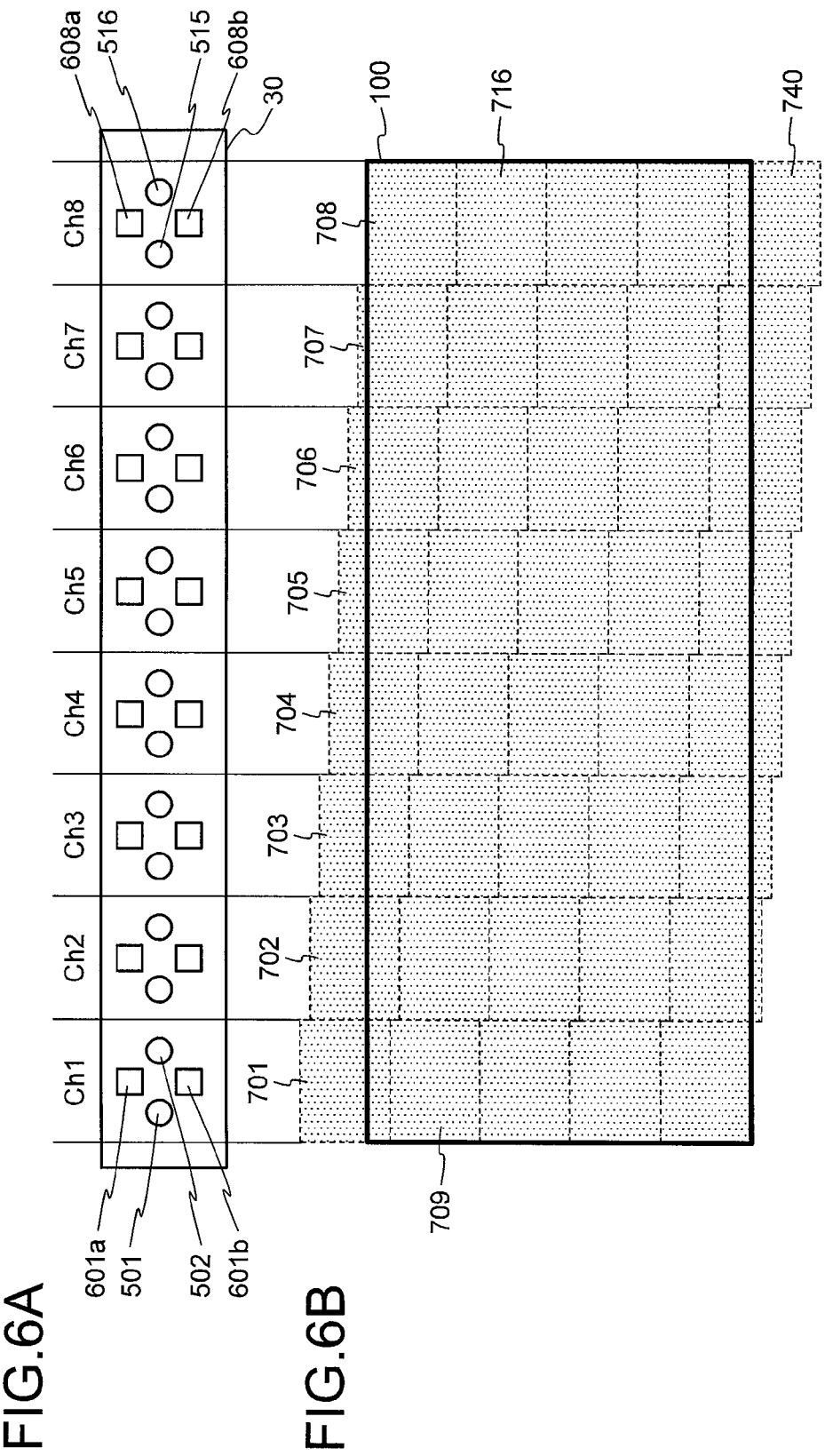

FIG.6C

| No. | BANK-NOTE POSITION (mm) | SENSOR | | | FIRST LIGHT SOURCE (UV) | | | | SECOND LIGHT SOURCE (IR) | | | |
|---|---|---|---|---|---|---|---|---|---|---|---|---|
| | | MEA-SUREMENT START (μs) | MEA-SUREMENT DURATION (μs) | GAIN | LIGHT-ING Ch | LIGHTING START (μs) | LIGHTING DURA-TION (μs) | EMISSION CURRENT VALUE (mA) | LIGHT-ING Ch | LIGHTING START (μs) | LIGHTING DURA-TION (μs) | EMISSION CURRENT VALUE (mA) |
| 0 | 0 | 0 | 500 | 1 | 1 | 0 | 500 | 10 | 0 | 0 | 0 | 0 |
| 1 | 1 | 0 | 500 | 1 | 2 | 0 | 500 | 10 | 0 | 0 | 0 | 0 |
| 2 | 2 | 0 | 500 | 1 | 3 | 0 | 500 | 10 | 0 | 0 | 0 | 0 |
| 3 | 3 | 0 | 500 | 1 | 4 | 0 | 500 | 10 | 0 | 0 | 0 | 0 |
| 4 | 4 | 0 | 500 | 1 | 5 | 0 | 500 | 10 | 0 | 0 | 0 | 0 |
| 5 | 5 | 0 | 500 | 1 | 6 | 0 | 500 | 10 | 0 | 0 | 0 | 0 |
| 6 | 6 | 0 | 500 | 1 | 7 | 0 | 500 | 10 | 0 | 0 | 0 | 0 |
| 7 | 7 | 0 | 500 | 1 | 8 | 0 | 500 | 10 | 0 | 0 | 0 | 0 |
| 8 | 8 | 0 | 500 | 1 | 1 | 0 | 500 | 10 | 0 | 0 | 0 | 0 |
| ... | | | | | | | | | | | | |

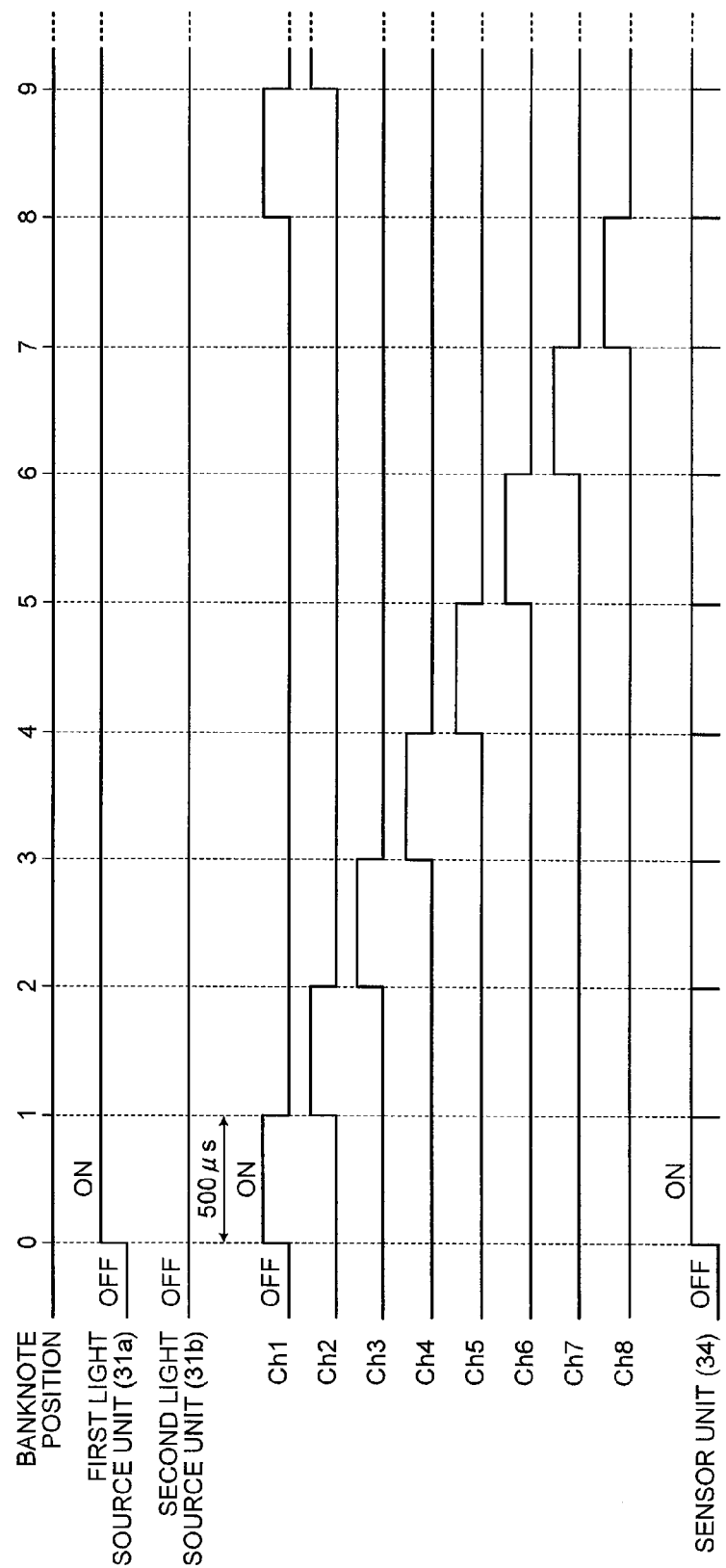

FLUORESCENCE EMITTED
BY UV LIGHT IRRADIATION

FLUORESCENCE EMITTED
BY UV LIGHT IRRADIATION

FLUORESCENCE EMITTED
BY UV LIGHT IRRADIATION

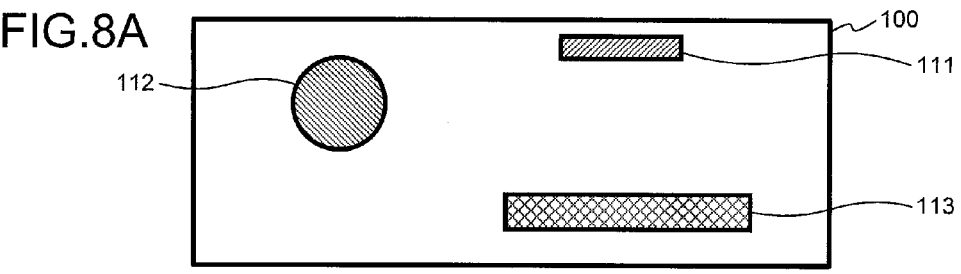
FIG.8A
FIG.8B
REFLECTED LIGHT EMITTED BY IR LIGHT IRRADIATION
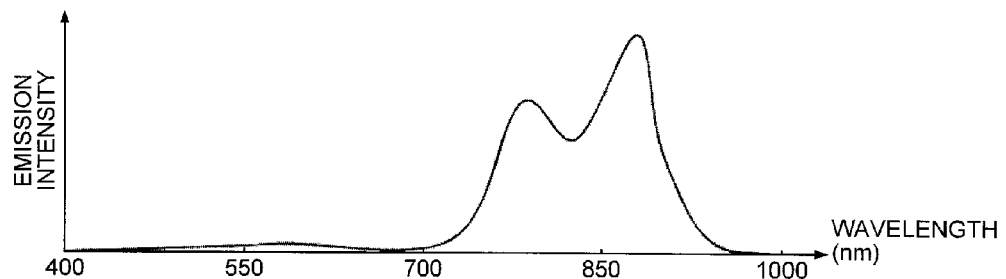
FIG.8C
FLUORESCENCE EMITTED BY UV LIGHT IRRADIATION
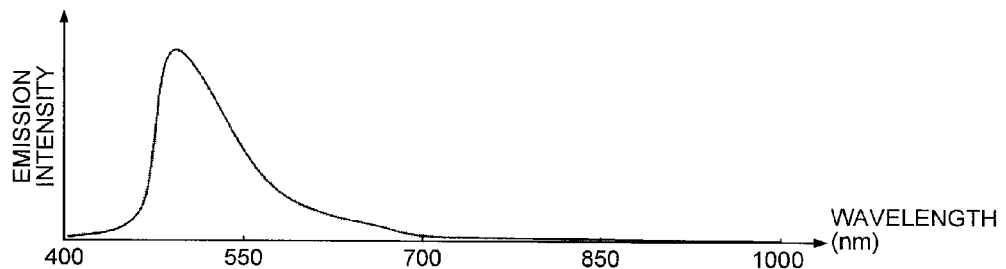
FIG.8D
FLUORESCENCE EMITTED BY UV LIGHT IRRADIATION AND
REFLECTED LIGHT EMITTED BY IR LIGHT IRRADIATION
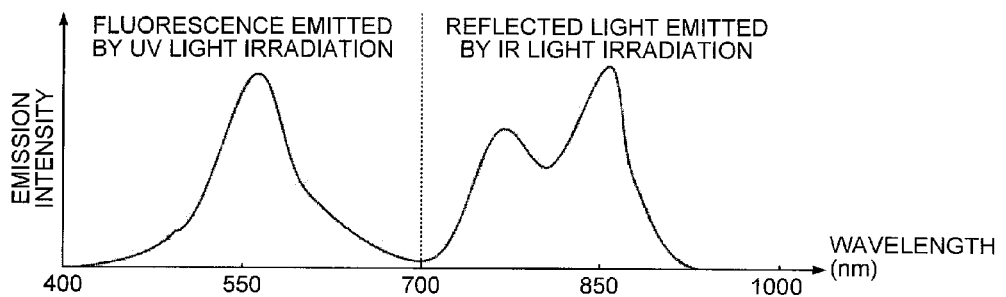

FIG.9B

| No. | BANK-NOTE POSI-TION (mm) | SENSOR | | | FIRST LIGHT SOURCE (UV) | | | | SECOND LIGHT SOURCE (IR) | | | |
|---|---|---|---|---|---|---|---|---|---|---|---|---|
| | | MEA-SURE-MENT START (μs) | MEA-SURE-MENT DURATION (μs) | GAIN | LIGHT-ING Ch | LIGHTING START (μs) | LIGHTING DURA-TION (μs) | EMISSION CURRENT VALUE (mA) | LIGHT-ING Ch | LIGHTING START (μs) | LIGHTING DURA-TION (μs) | EMISSION CURRENT VALUE (mA) |
| 0 | 4 | 0 | 500 | 1 | 0 | 0 | 0 | 0 | 5 | 0 | 500 | 10 |
| 1 | 5 | 0 | 500 | 1 | 0 | 0 | 0 | 0 | 6 | 0 | 500 | 10 |
| 2 | 6 | 0 | 500 | 1 | 0 | 0 | 0 | 0 | 7 | 0 | 500 | 10 |
| 3 | 9 | 0 | 500 | 1 | 2 | 0 | 500 | 10 | 0 | 0 | 0 | 0 |
| 4 | 10 | 0 | 500 | 1 | 3 | 0 | 500 | 10 | 0 | 0 | 0 | 0 |
| 5 | 17 | 0 | 500 | 1 | 2 | 0 | 500 | 10 | 0 | 0 | 0 | 0 |
| 6 | 18 | 0 | 500 | 1 | 3 | 0 | 500 | 10 | 0 | 0 | 0 | 0 |
| 7 | 28 | 0 | 500 | 1 | 5 | 0 | 500 | 10 | 5 | 0 | 500 | 10 |
| 8 | 29 | 0 | 500 | 1 | 6 | 0 | 500 | 10 | 6 | 0 | 500 | 10 |
| 9 | 30 | 0 | 500 | 1 | 7 | 0 | 500 | 10 | 7 | 0 | 500 | 10 |
| ... | | | | | | | | | | | | |

BANKNOTE IMAGE BASED ON UV LIGHT IRRADIATION

BANKNOTE IMAGE BASED ON IR LIGHT IRRADIATION

FIG.11B FLUORESCENCE EMITTED BY UV LIGHT IRRADIATION

FIG.11C FLUORESCENCE AND PHOSPHORESCENCE EMITTED BY UV LIGHT IRRADIATION

FIG.11D PHOSPHORESCENCE EMITTED BY IR LIGHT IRRADIATION

FIG.11E PHOSPHORESCENCE EMITTED BY UV LIGHT IRRADIATION AND PHOSPHORESCENCE EMITTED BY IR LIGHT IRRADIATION

FIG.12B

| No. | BANK-NOTE POSI-TION (mm) | SENSOR | | | FIRST LIGHT SOURCE (UV) | | | | SECOND LIGHT SOURCE (IR) | | | |
|---|---|---|---|---|---|---|---|---|---|---|---|---|
| | | MEA-SURE-MENT START (μs) | MEA-SURE-MENT DURATION (μs) | GAIN | LIGHT-ING Ch | LIGHTING START (μs) | LIGHTING DURA-TION (μs) | EMISSION CURRENT VALUE (mA) | LIGHT-ING Ch | LIGHTING START (μs) | LIGHTING DURA-TION (μs) | EMISSION CURRENT VALUE (mA) |
| 0 | 9 | 0 | 500 | 1 | 2 | 0 | 500 | 10 | 0 | 0 | 0 | 0 |
| 1 | 10 | 0 | 500 | 1 | 3 | 0 | 500 | 10 | 0 | 0 | 0 | 0 |
| 2 | 19 | 500 | 500 | 2 | 0 | 0 | 0 | 0 | 0 | 0 | 0 | 0 |
| 3 | 19 | 500 | 500 | 2 | 0 | 0 | 0 | 0 | 4 | 0 | 500 | 10 |
| 4 | 29 | 400 | 500 | 2 | 6 | 0 | 400 | 10 | 6 | 0 | 400 | 10 |
| ... | | | | | | | | | | | | |

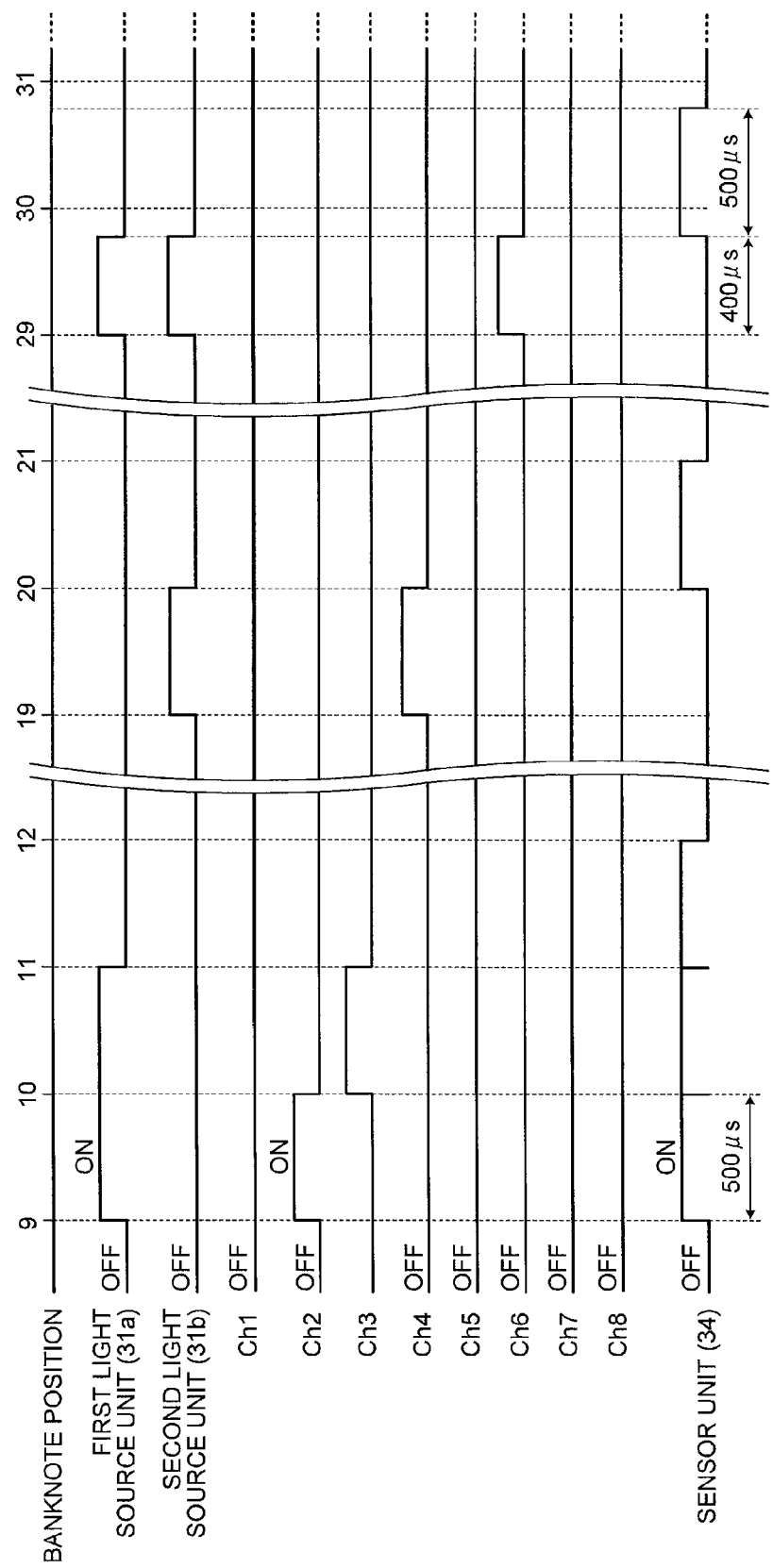

FLUORESCENT BANKNOTE IMAGE BASED ON UV LIGHT IRRADIATION

PHOSPHORESCENT BANKNOTE IMAGE BASED ON UV LIGHT IRRADIATION

PHOSPHORESCENT BANKNOTE IMAGE BASED ON IR LIGHT IRRADIATION

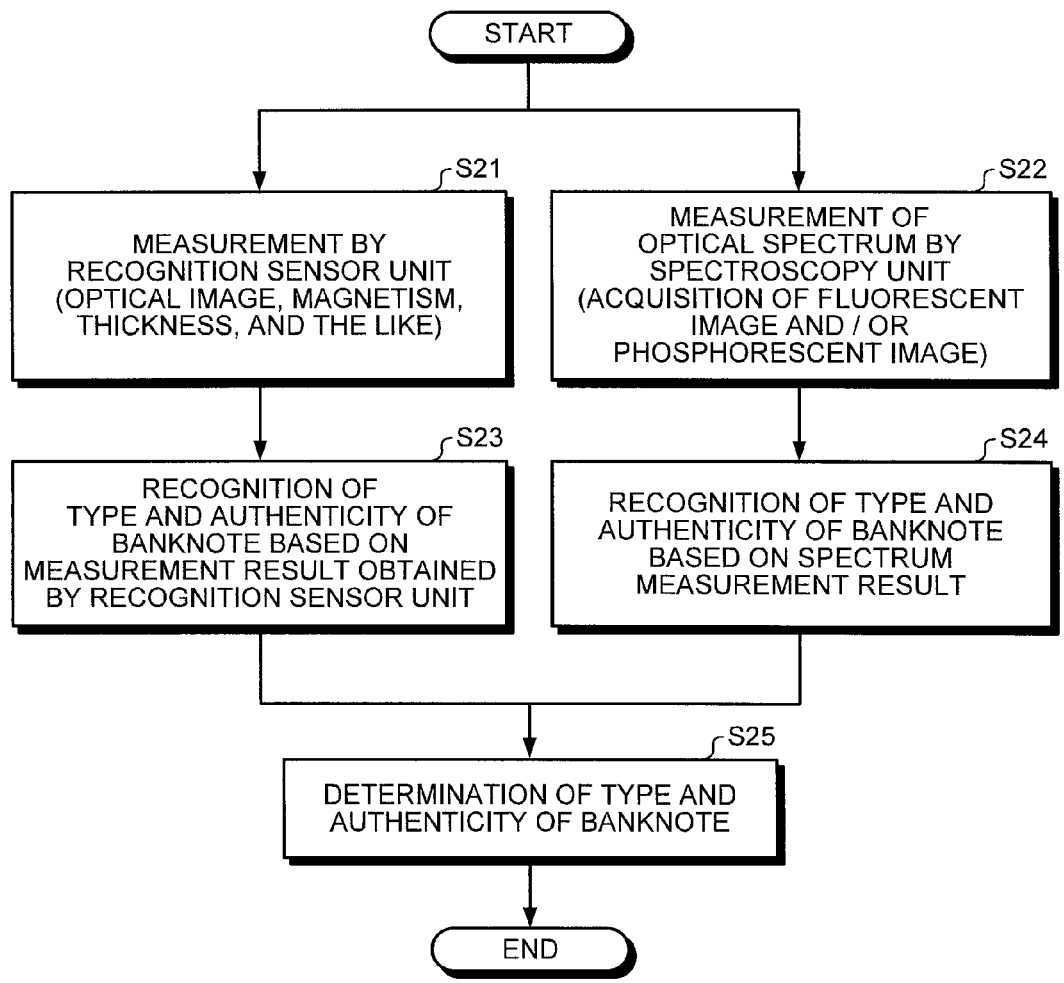

PAPER SHEET RECOGNITION APPARATUS AND PAPER SHEET RECOGNITION METHOD

TECHNICAL FIELD

The present invention relates to a paper sheet recognition apparatus and a paper sheet recognition method that acquire optical characteristics of a paper sheet to recognize the paper sheet.

BACKGROUND ART

A paper sheet recognition apparatus that acquires an image and a spectrum of optical characteristics of a paper sheet, and recognizes a type and authenticity of the paper sheet based on the acquired information is known in the art. For example, Patent Document 1 discloses an apparatus that irradiates a paper sheet with a light of a predetermined wavelength, and recognizes authenticity of the paper sheet based on a feature appearing in optical spectrums of fluorescence and phosphorescence that are excited on the paper sheet. Moreover, Patent Document 2 discloses an apparatus in which a plurality of light sources capable of irradiating a paper sheet with lights varying in the angles of irradiation are arranged, and presence or absence of a hologram on the paper sheet is determined based on a difference in reflection spectrums obtained by emitting lights from these light sources. In this apparatus, authenticity of the paper sheet is recognized from the presence or absence of the hologram on the paper sheet.

CITATION LIST

Patent Document

Patent Document 1: Japanese Patent Application Laid-Open No. 2006-275578
Patent Document 2: Japanese Patent Application Laid-Open No. 2009-181403

SUMMARY OF INVENTION

Technical Problem

However, in the above conventional technique, there are situations in which all the optical characteristics necessary for the recognition of the paper sheet may not be acquired efficiently. There is a need to acquire optical characteristics from a plurality of partial areas on one paper sheet, such as a partial area in which emission of fluorescence is observed, a partial area in which emission of phosphorescence is observed, a partial area in which a hologram is observed, and the like, on a paper sheet, to recognize the paper sheet; however, the conventional technique does not cope with this need. For example, if a sensor and a light source are arranged for each of the plurality of partial areas, the production cost and the apparatus size of the paper sheet recognition apparatus increase. Therefore, there is a need of a paper sheet recognition apparatus that can efficiently acquire optical characteristics from a plurality of partial areas that are at spaced-apart positions on a paper sheet while suppressing the production cost and the apparatus size.

The present invention is made to solve problems in the conventional technology. One object of the present invention is to provide a paper sheet recognition apparatus and a paper sheet recognition method that can efficiently acquire optical characteristics from a plurality of partial areas on a paper sheet.

Means for Solving Problems

To solve the above problem, and to achieve the above object, a paper sheet recognition apparatus according to one aspect of the present invention, which recognizes a paper sheet by using an optical spectrum acquired from the paper sheet by emitting a light on the paper sheet transported on a transport path, includes a light source unit including a plurality of light sources arranged corresponding to a plurality of partial areas on the paper sheet; a reading unit having a light receiving surface that is arranged so as to receive reflected lights from the plurality of partial areas; a sensor unit that acquires an optical spectrum from the light received by the light receiving surface; a memory that stores therein an optical spectrum measurement condition including a plurality of pieces of information associated with each other for acquiring the optical spectrum from a predetermined partial area on the paper sheet, the plurality of pieces of information including information for identifying at least one light source corresponding to the predetermined partial area among the light sources of the light source unit, information for identifying a timing for turning on the identified light source, and information for identifying a timing for turning off the light source that is turned on at the timing for turning on; and a light-source control unit that controls the light source unit based on the optical spectrum measurement condition. The light source emits a light on the pater sheet to acquire a reflected light from the paper sheet, to acquire a transmitted light that has passed through the paper sheet, to excite fluorescence on the paper sheet, to excite phosphorescence on the paper sheet, and the like.

In the above paper sheet recognition apparatus, the plurality of pieces of information associated with each other stored in the optical spectrum measurement condition in the memory further includes information for identifying an emission quantity when the identified light source is turned on.

In the above paper sheet recognition apparatus, the plurality of pieces of information associated with each other stored in the optical spectrum measurement condition in the memory further includes information for identifying a timing to start the acquisition of the optical spectrum by the sensor unit, and information for identifying a timing to stop the acquisition of the optical spectrum.

In the above paper sheet recognition apparatus, the plurality of pieces of information associated with each other stored in the optical spectrum measurement condition in the memory further includes information for identifying an adjustment amount of a signal gain for acquiring the optical spectrum by the sensor unit.

In the above paper sheet recognition apparatus, the optical spectrum measurement condition is prepared for each type and each orientation of the paper sheet, in the memory, and the light-source control unit reads from the memory the optical spectrum measurement condition corresponding to a type and an orientation of the paper sheet that is being transported on the transport path and controls the light source unit.

In the above paper sheet recognition apparatus, the light source unit is capable of emitting at least two types of lights having different wavelength bands, and the information for identifying the light source in the optical spectrum measurement condition includes information to identify a type of the light.

In the above paper sheet recognition apparatus, the light source unit includes one light source that emits a light from an upstream side in a transport direction to a light receiving area on the paper sheet; and another light source that emits the light from a downstream side in the transport direction to the light receiving area.

In the paper sheet recognition apparatus, an image of the partial area is generated based on the optical spectrum acquired from the partial area by the sensor unit, and a paper sheet image indicating optical characteristics of the paper sheet is generated from the image of the partial area.

According to another aspect of the present invention, a paper sheet recognition method for recognizing a paper sheet by using an optical spectrum acquired from the paper sheet transported on a transport path includes acquiring an optical spectrum measurement condition that includes a plurality of pieces of information associated with each other, the plurality of pieces of information including information for identifying at least one light source corresponding to a partial area from which an optical spectrum is acquired among a plurality of light sources included in a light source unit, information for identifying a timing for turning on the identified light source, and information for identifying a timing for turning off the light source that is turned on at the timing for turning on; controlling the light source unit based on the acquired optical spectrum measurement condition; receiving a light from a plurality of partial areas on the paper sheet by a light receiving surface of a reading unit; and acquiring an optical spectrum by a sensor unit from the light received by the light receiving surface.

Advantageous Effects of Invention

According to the present invention, a plurality of light sources capable of emitting a light in a plurality of partial areas on a paper sheet are provided, and each of the light sources is controlled based on an optical spectrum measurement condition in which a light source to be turned on from among those plurality of light sources, a timing to turn on the light source, a timing to turn off the turned on light source, and the like, are set. As a result, for example, in a paper sheet recognition apparatus capable of receiving a light with a reading unit from an entire area on a paper sheet in a main scanning direction and acquiring an optical spectrum with a sensor unit from the received light, it is possible to irradiate only a desired partial area on the paper sheet with the light and acquire the optical spectrum only from that partial area. It is possible to acquire an optical spectrum from each of a plurality of partial areas on the paper sheet that is transported on a transport path by setting an optical spectrum measurement condition. For example, it is possible to acquire optical spectrums simultaneously from each of a plurality of partial areas that are at spaced-apart positions in the main scanning direction. It is also possible to acquire optical spectrums sequentially from the entire surface of the paper sheet by alternately turning on/off the light sources.

Moreover, according to the present invention, because an emission quantity when the identified light source is turned on can be set in the optical spectrum measurement condition, the emission quantity of the light emitted from the light source can be adjusted depending on the luminous phenomenon excited on the paper sheet.

Furthermore, according to the present invention, because a timing to start the acquisition of the optical spectrum can be set in the optical spectrum measurement condition, for example, the optical spectrums of both of fluorescence and phosphorescence can be acquired from the same partial area.

Moreover, according to the present invention, because a signal gain when the optical spectrum is acquired can be set in the optical spectrum measurement condition, for example, even if the emission intensity of the phosphorescence is weak, the signal gain can be adjusted so that features, such as a peak, can appear on the signal waveform of the acquired optical spectrum.

Furthermore, according to the present invention, because an optical spectrum can be acquired only from a partial area necessary to recognize this paper sheet based on a recognition result about a type and an orientation of a paper sheet obtained, for example, by using a conventional line sensor, a conventional magnetic sensor, a conventional thickness sensor, and the like, a processing load for the acquisition of the optical spectrum can be reduced.

Moreover, according to the present invention, because a type of the light to be emitted on a paper sheet can be specified as the optical spectrum measurement condition, it is possible to select a light necessary to excite emission in each partial area from among, for example, an ultraviolet light, an infrared light, and the like.

Furthermore, according to the present invention, when emitting a light on a paper sheet, because a light can be emitted from each of an upstream side and a downstream side in a transport direction with respect to a partial area on the paper sheet from which an optical spectrum is to be acquired, a light can be emitted and emission can be excited surely even when the paper sheet has, for example, a crumble or a crease.

According to the present invention, a paper sheet image that reflects a feature appearing in an optical spectrum can be generated by using an optical spectrum acquired from the paper sheet. Therefore, for example, a denomination, authenticity, and the like, of a banknote can be recognized based on a comparison of such a paper sheet image with banknote images prepared previously depending on a denomination, authenticity, and the like, of the banknote.

BRIEF DESCRIPTION OF DRAWINGS

FIGS. 6A, 6B, 6C and 6D are views for explaining a method of acquiring data relating to optical characteristics from an entire surface of a banknote.

FIGS. 8A, 8B, 8C, and 8D are views of an example of a banknote on which emission of fluorescence are observed in three partial areas.

FIGS. 9A, 9B, and 9C are views for explaining an optical spectrum measurement condition set for the banknote shown in FIG. 8A.

FIGS. 11A, 11B, 11C, 11D, and 11E are views of an example of a banknote on which emission of fluorescence and phosphorescence are observed.

FIGS. 12A, 12B, and 12C are views explaining an optical spectrum measurement condition set for the banknote shown in FIG. 11A.

FIG. 15 is a flowchart indicating a situation in which the process by the recognition sensor unit and the process by the spectroscopy unit are performed in parallel.

DESCRIPTION OF EMBODIMENTS

Figure 1:
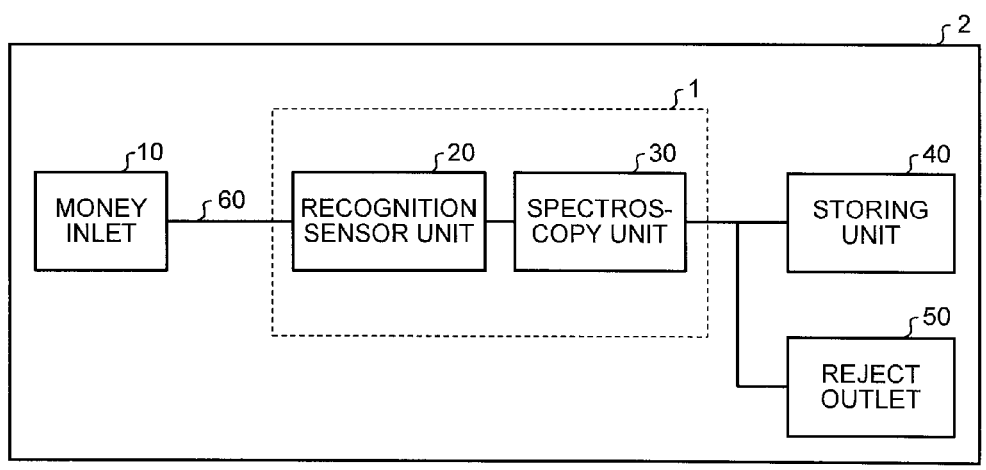
FIG. 1 is a schematic block diagram of a configuration example of a banknote handling apparatus that uses as a recognition unit a paper sheet recognition apparatus according to the present embodiment.

Exemplary embodiments of a paper sheet recognition apparatus and a paper sheet recognition method according to the present invention are explained below with reference to the accompanying drawings. The paper sheet recognition apparatus according to the present invention has a function to recognize a type, authenticity, fitness, and the like, of a paper sheet based on optical characteristics of the paper sheet acquired by a spectroscopy unit.

At first, an outline of the paper sheet recognition apparatus is explained. In the paper sheet recognition apparatus, at least one light source is specified from among a plurality of light sources, which are arranged along a main scanning direction of a sensor that acquires an optical spectrum, for emitting a light on a partial area, which is a measurement target, from among a plurality of partial areas. The partial areas are obtained by dividing a paper sheet into a plurality of areas. A type (wavelength), an emission quantity, a timing to start the emission, a duration time, and the like, of the light to be emitted from the light source can be controlled. Accordingly, a desired partial area on the paper sheet can be irradiated with the light and an optical spectrum of a light excited in that partial area can be acquired. At this time, by controlling an on-timing and an off-timing of the light source and a timing of acquiring a signal from the sensor, one or both of fluorescence and phosphorescence can be selected as a measurement target. Moreover, in the paper sheet recognition apparatus, it is possible to adjust one or both of a current value and an emission duration to control an emission quantity of the light emitted from the light source so that features such as a peak appearing on a signal waveform of the optical spectrum becomes clear. Moreover, it is possible to adjust one or both of a gain and a measurement duration of a signal obtained by measuring with a sensor a light excited on the paper sheet. The light source emits a light to acquire a reflected light from a paper sheet, to acquire a transmitted light that has passed through a paper sheet, to excite fluorescence on a paper sheet, to excite phosphorescence on a paper sheet, and the like. In the paper sheet recognition apparatus, by controlling the light source and the sensor, one or more among a reflection spectrum, an absorption spectrum, a transmission spectrum, a fluorescence spectrum, and a phosphorescence spectrum can be acquired as the optical spectrum. In the following discussion, mainly an example is explained in which an excitation light is emitted on a paper sheet from a light source and an optical spectrum of the excited light is measured.

The paper sheet recognition apparatus can handle various types of paper sheets such as a banknote, a check, other valuable securities, and the like, as a processing object. However, in the following explanation, a situation is explained in which the paper sheet recognition apparatus is used as a recognition unit in a banknote handling apparatus that handles a banknote as a processing object.

FIG. 1 is a schematic block diagram of a configuration of a banknote handling apparatus 2 that uses a paper sheet recognition apparatus 1 (hereinafter, "recognition unit 1") according to the present embodiment. The banknote handling apparatus 2 includes a money inlet 10, a transport path 60, the recognition unit 1, a storing unit 40, and a reject outlet 50. A plurality of banknotes can be set in the money inlet 10. The transport path 60 transports banknotes fed one by one in the apparatus from the money inlet 10. The recognition unit 1 recognizes a denomination, authenticity, fitness, and the like, of the banknote transported by the transport path 60. The storing unit 40 stores therein a banknote that is recognized as being storable in the apparatus based on a recognition result obtained by the recognition unit 1. A reject banknote, such as a banknote that cannot be recognized in the recognition unit 1, or a counterfeit banknote, is rejected from the reject outlet 50.

The recognition unit 1 includes a recognition sensor unit 20 that includes a line sensor that acquires an image of the banknote, a magnetic sensor that acquires a magnetic characteristic of the banknote, a thickness sensor that measures a thickness of the banknote, and the like, and a spectroscopy unit 30 that acquires an optical spectrum. Because a conventional technique can be used for a recognition processing of the banknote performed in the recognition unit 1 by using the recognition sensor unit 20, and a banknote handling performed in the banknote handling apparatus 2 based on the recognition result, a detailed explanation of these processings will be omitted, and the spectroscopy unit 30 will be explained in detail below.

Figure 2A:
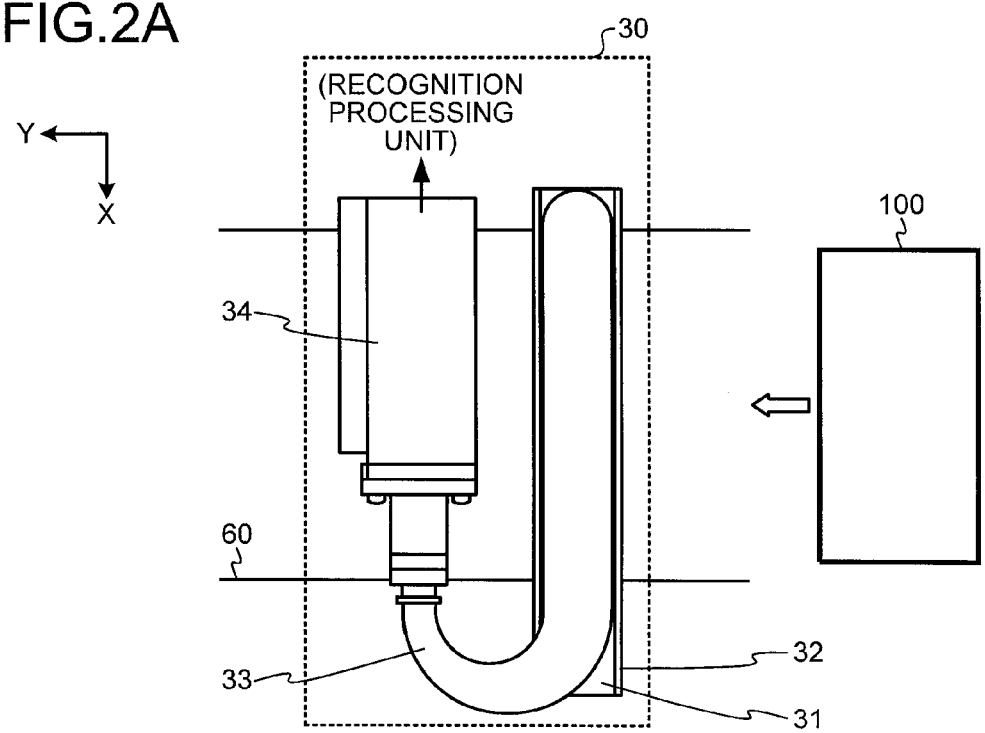
FIGS. 2A and 2B are external views of a configuration of a spectroscopy unit.
Figure 2B:
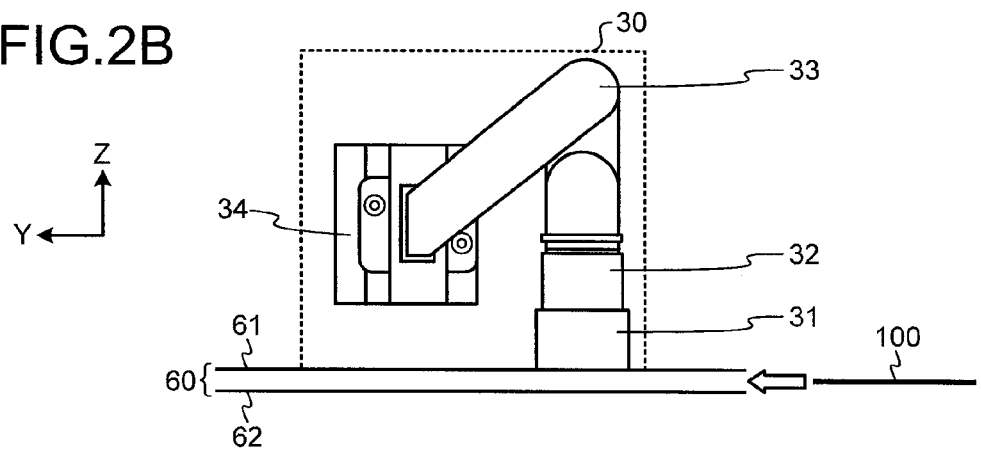

FIGS. 2A and 2B are external views for explaining a configuration of the spectroscopy unit 30. FIG. 2A is a plan view seen from an upper side (positive Z-axis direction) of the transport path 60, and FIG. 2B is a plan view seen from a side (positive X-axis direction) of the transport path. As shown in FIG. 2B, a banknote 100 is transported between an upper guide 61 and a lower guide 62 constituting the transport path 60. The spectroscopy unit 30 includes a light source unit 31, a reading unit 32, a light guide unit 33, and a sensor unit 34.

To acquire an optical spectrum from a light received from the banknote 100 that is transported on the transport path 60, each of the light source unit 31, the reading unit 32, and the sensor unit 34 are arranged within a box-shaped casing made from black resin, metal, and the like, that do not pass light, so that noise light does not enter from the outside. The light guide unit 33 connects the reading unit 32 and the sensor unit 34, which is arranged at a spaced-apart position from the reading unit 32, and guides the light received by the reading unit 32 to the sensor unit 34. The light guide unit 33 is bendable and arranged within a cylindrical casing made from black soft resin, fiber, and the like, that do not pass light, so that noise light does not enter the light guide unit 33. Accordingly, in the spectroscopy unit 30, only the light received by the reading unit 32 is guided to the sensor unit 34 via the light guide unit 33.

The reading unit 32 is arranged above the transport path 60 such that a main scanning direction thereof is orthogonal to a transport direction (hollow arrow in FIGS. 2A and 2B) of the banknote 100. The light source unit 31 is arranged corresponding to a reading area, from which the reading unit 32 reads the optical characteristics of the banknote 100, so as to emit a light in the reading area. An arrangement position of the sensor unit 34 that acquires the optical spectrum from the light received by the reading unit 32 is not particularly limited. That is, the sensor unit 34 can be arranged at a desired position at which the bendable light guide unit 33 can guide the light received by the reading unit 32 to the sensor unit 34. Data of the optical spectrum obtained by the sensor unit 34 is input into a recognition processing unit (see FIG. 5) that recognizes a denomination, authenticity, fitness, and the like of the banknote 100. A transmission spectrum and an absorption spectrum of the banknote 100, which is transported on the transport path 60, can be acquired by arranging the light source unit 31 on the lower side (negative Z-axis direction) of the transport path 60 with respect to the spectroscopy unit 30 that is arranged on the upper side (positive Z-axis direction) of the transport path 60. In the following explanation, as shown in FIG. 2B, both the spectroscopy unit 30 and the light source unit 31 are arranged on the upper side of the transport path 60, and a situation in which a reflection spectrum of a top surface of the banknote 100 is acquired is explained as an example.

Figure 3A:
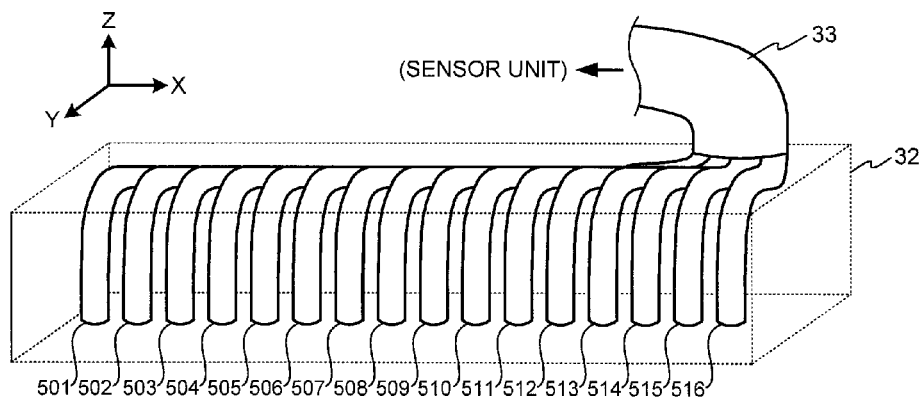
FIGS. 3A, 3B, and 3C are schematic diagrams of configurations of a light source unit and a reading unit.
Figure 3B:
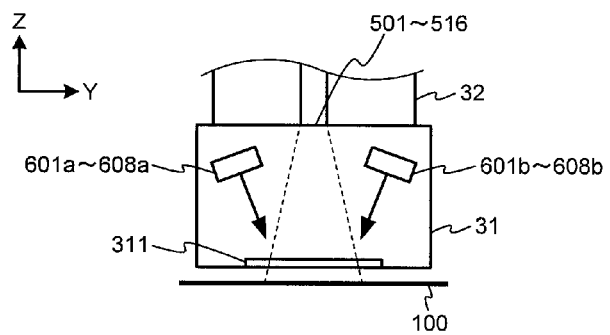
Figure 3C:
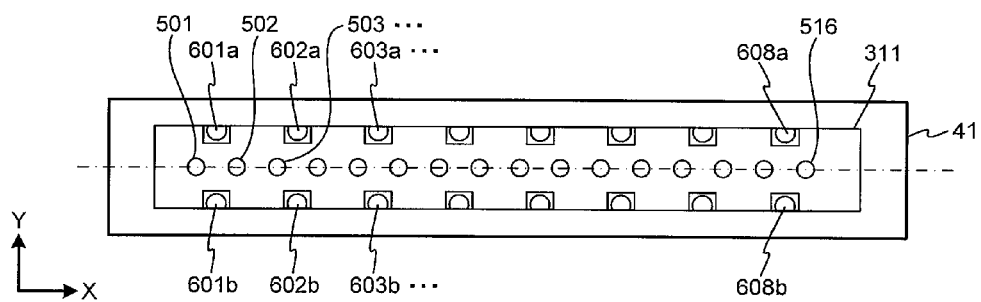

FIGS. 3A to 3C are schematic diagrams of configurations of the light source unit 31 and the reading unit 32. FIG. 3A is a perspective view of an internal structure of the reading unit 32, FIG. 3B is a sectional view when the inside of the light source unit 31 is seen from a negative X-axis direction, and FIG. 3C is a plan view of a bottom surface of the light source unit 31 that opposes the transport path 60 when seen from the negative Z-axis direction.

As shown in FIG. 3A, in the reading unit 32, light receiving surfaces 501 to 516 of 16 units of optical fibers that receive the light from the banknote 100 are arranged at a regular interval on a line along the X axis direction whereby the light can be received from the entire surface of the banknote 100 in the main scanning direction (X axis direction). The light guide unit 33 is formed by bundling those 16 units of the optic fibers. The lights received from the light receiving surfaces 501 to 516 from one ends of the optic fibers are guided from the other ends of the optic fibers to the sensor unit 34 via the optic fibers constituting the light guide unit 33.

As shown in FIG. 3B, a transparent member 311 enabling emission of a light on the banknote 100 and reception of light from the banknote 100 is fitted on a bottom surface of the light source unit 31. Each of the light receiving surfaces 501 to 516 of the reading unit 32 is fixed so as to expose to the outside from a bottom surface of the reading unit 32. The light emitted from a plurality of light sources 601a to 608a and 601b to 608b constituting the light source unit 31 passes through the transparent member 311 and then is emitted on the banknote 100. The light reflected from the banknote 100 passes through the transparent member 311 and is received in the light receiving surfaces 501 to 516 of the reading unit 32.

As shown in FIG. 3C, the eight light sources 601a to 608a arranged at a regular interval on a line along the X axis direction and the eight light sources 601b to 608b arranged at a regular interval on a line along the X axis direction are arranged symmetrically with respect to a line (dashed line in figure) on which the 16 units of the light receiving surfaces 501 to 516 are arranged. The 16 units of the light sources 601a to 608a and 601b to 608b, and the 16 units of the light receiving surfaces 501 to 516 are grouped in eight groups each including two light sources and two light receiving surfaces. Specifically, for example, the light receiving surfaces 501 and 502 that are adjacent to each other, and one light source 601a arranged on a positive Y-axis direction and one light source 601b arranged on a negative Y-axis direction form one group. The light source 601a and the light source 601b are positioned on a central line that passes between the light receiving surface 501 and the light receiving surface 502 and that is parallel to the Y axis. A distance from the light receiving surface 501 to the light source 601a, a distance from the light receiving surface 501 to the light source 601b, a distance from the light receiving surface 502 to the light source 601a, and a distance from the light receiving surface 502 to the light source 601b are all equal. The two light receiving surfaces and the two light sources of all the eight groups are arranged in the similar manner.

One or more light emitting elements, such as LEDs, are used as the light sources 601a to 608a and 601b to 608b. For example, one light emitting element that emits a light of only one wavelength can be used as the light source 601a. Alternatively, a plurality of light emitting elements that emit lights of different wavelengths can be used as the light source 601a. Alternatively, one light emitting element capable of emitting lights of different wavelengths can be used as the light source 601a. The type of the light emitting element to use is determined based on the type of the light necessary to excite emission from the banknote 100. In the following explanation, each of the light sources 601a to 608a and 601b to 608b is capable of emitting one or both of an infrared light and an ultraviolet light.

Figure 4A:
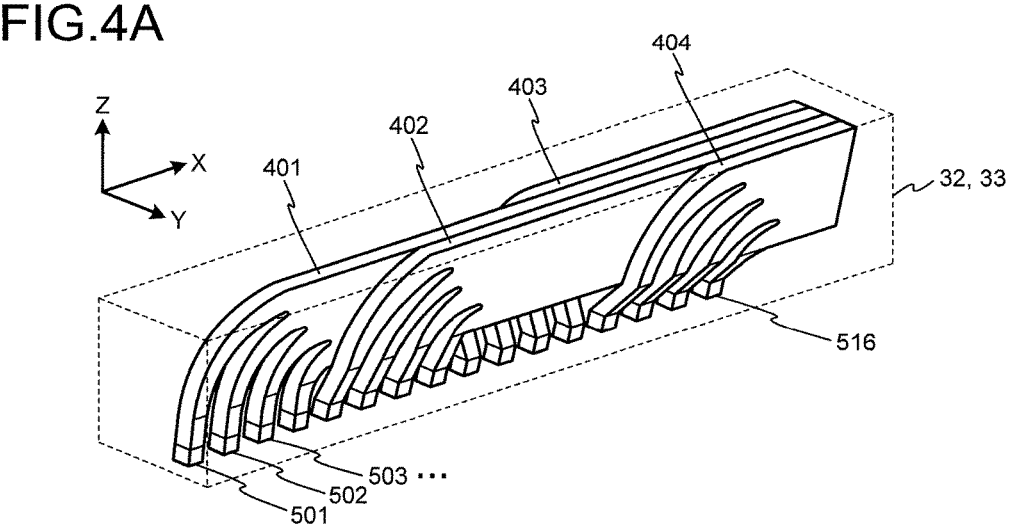
FIGS. 4A, 4B, and 4C are schematic diagrams of an example in which the reading unit and a light guide unit are formed by a plurality of light guiding plates.
Figure 4B:
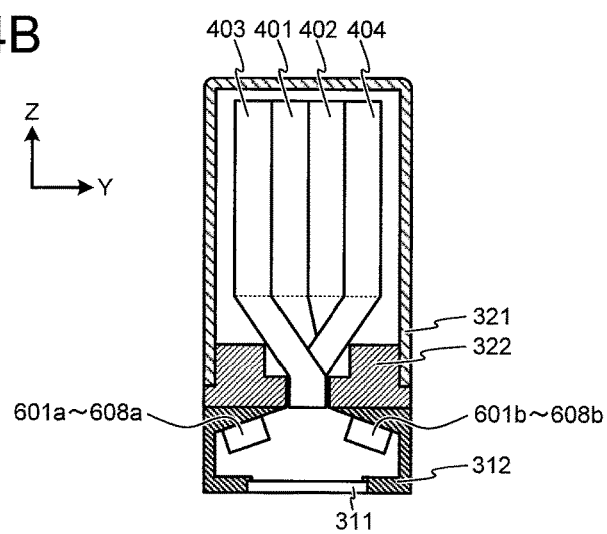
Figure 4C:
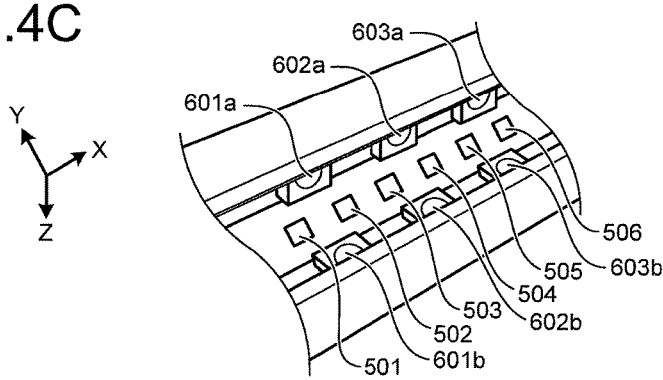

FIGS. 3A to 3C show an example in which the reading unit 32 and the light guide unit 33 are constituted by a plurality of the optical fibers; however, the present embodiment is not limited to this example. FIGS. 4A to 4C are schematic diagrams of an example in which the reading unit 32 and the light guide unit 33 are constituted by a plurality of light guiding plates 401 to 404. In this example, as shown in FIG. 4B, the four light guiding plates 401 to 404 are supported by a base member 322 and accommodated inside a cover member 321. As shown in FIG. 4A, each of the light guiding plates 401 to 404 has four light receiving surfaces, and these light receiving surfaces constitute the 16 units of the light receiving surfaces 501 to 516 of the reading unit 32. The light source unit 31, which includes the transparent member 311 and a casing 312, includes the plurality of light sources 601a to 608a and 601b to 608b. As shown in FIG. 4C, each of the light sources 601a to 608a and 601b to 608b and each of the light receiving surfaces 501 to 516 are arranged with the same positional relationship as that shown in FIG. 3C.

Upon receiving the light received by the reading unit 32 and guided thereto by the light guide unit 33, the sensor unit 34 separates this light into an extraordinary light and an ordinary light by using a scatterplate, a first 45-degree polarizing plate, Wollaston prism, and a second 45-degree polarizing plate, and focuses the light with a lens on a CCD sensor to acquire the optical spectrum.

Because structures and functions of the light guiding plates 401 to 404 shown in FIG. 4, an optical processing method to obtain an interference fringe by the Wollaston prism from the light received from the banknote 100, and a method to capture the obtained interference fringe by using the CCD sensor to acquire the optical spectrum are explained in WO 2013/027848, a detailed explanation thereof will be omitted. A control method for acquiring the optical spectrum of the banknote 100 by using the spectroscopy unit 30 is explained below.

Figure 5:
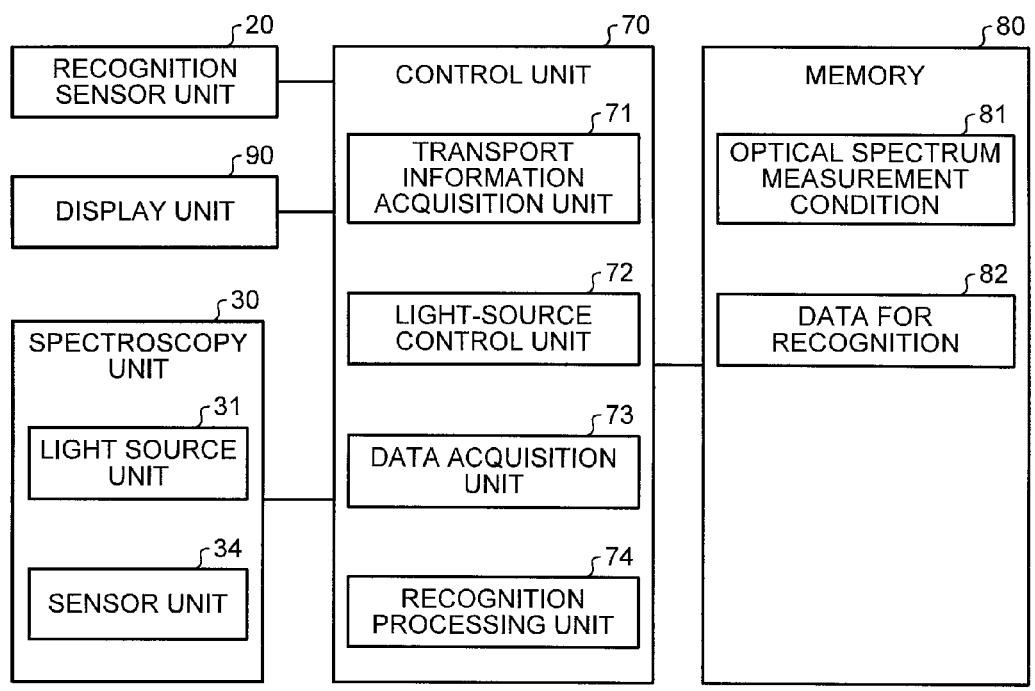
FIG. 5 is a block diagram of a functional configuration of the recognition unit.

FIG. 5 is a block diagram of a functional configuration of the recognition unit 1. The recognition unit 1 includes the recognition sensor unit 20 and the spectroscopy unit 30 shown in FIG. 1, a control unit 70, a memory 80, and a display unit 90 that can display an optical spectrum, a banknote image, and the like. The control unit 70 includes a transport information acquisition unit 71, a light-source control unit 72, a data acquisition unit 73, and a recognition processing unit 74. A function and an operation of all the components related to a function and an operation of the spectroscopy unit 30 are explained below.

The transport information acquisition unit 71 acquires transport information of the banknote 100 on the transport path 60. The transport information acquisition unit 71 includes a function to identify a transport position of the banknote 100 on the transport path 60. For example, the transport position of the banknote 100 on the transport path 60 is identified based on a transport speed of the banknote 100 transported by transport rollers and a transport belt, a detection result obtained by a detection sensor that detects passage of the banknote at a predetermined position in the transport path 60, and the like. The timing at which the banknote 100 passes a reading area, which is an area on the transport path 60 on which a light is emitted from the light source unit 31 and from which light is read by the reading unit 32, can be identified by using a function of the transport information acquisition unit 71.

The light-source control unit 72 includes a function that controls an operation of the light source unit 31 based on the transport position of the banknote 100 on the transport path 60 identified by the transport information acquisition unit 71. Specifically, the light-source control unit 72 selects the LED(s) to be turned on among a plurality of LEDs and the like that are included in the light source unit 31 as the light sources 601a to 608a and 601b to 608b, to emit a light on the banknote 100 at the timing when the banknote 100 passes the reading area of the light receiving surfaces 501 to 516 of the reading unit 32. Moreover, the light-source control unit 72 controls the emission quantities of the LEDs by controlling timings to turn on the selected LEDs, lighting durations of the LEDs, current values when the LEDs are turned on, and the like.

The data acquisition unit 73 includes a function for acquiring data relating to features, such as an image, a magnetic characteristic, a thickness, of the banknote 100 by controlling an operation of the recognition sensor unit 20, which can include a line sensor, a magnetic sensor, a thickness sensor, and the like, based on the transport position of the banknote 100 on the transport path 60. The data acquisition unit 73 includes a function for acquiring data relating to optical characteristics of the banknote 100 by controlling an operation of the sensor unit 34 based on the position of the banknote 100 on the transport path 60 identified by the transport information acquisition unit 71. Moreover, the data acquisition unit 73 includes a function for adjusting one or both of a gain and a measurement duration of a signal output from the sensor unit 34 depending on the emission intensity of the light excited on the banknote 100.

In the recognition unit 1, even if the emission intensity of the light excited on the banknote 100 is weak, a signal strength of the optical spectrum acquired from the banknote 100 can be adjusted by adjusting, based on the emission intensity, one or more among a current value for controlling the emission quantity of the light to be emitted from the light source unit 31, a duration for emitting the light from the light source unit 31, a gain of the signal when measuring the light excited from the banknote 100 in the sensor unit 34, and a measurement duration for measuring the light by the functions of the light-source control unit 72 and the data acquisition unit 73.

The recognition processing unit 74 includes a function for recognizing a denomination, authenticity, and the like of the banknote 100 based on the data of the recognition sensor unit 20 acquired by the data acquisition unit 73. Moreover, the recognition processing unit 74 includes a function for recognizing a denomination, authenticity, and the like of the banknote 100 based on the data of the spectroscopy unit 30 acquired by the data acquisition unit 73.

The memory 80 is a nonvolatile storage device, such as a semiconductor memory, used for storing an optical spectrum measurement condition 81 and data for recognition 82. The light-source control unit 72 and the data acquisition unit 73 operate based on the optical spectrum measurement condition 81.

The data for recognition 82 stored in the memory 80 is used in order to recognize a denomination, authenticity, and the like of the banknote 100 based on the data acquired by the recognition sensor unit 20 and the spectroscopy unit 30. For example, the data to be obtained from the banknote 100 by using the recognition sensor unit 20, the data to be obtained from the banknote 100 by using the spectroscopy unit 30, and the like, are stored previously as the data for recognition 82 per denomination of the banknote 100. The recognition processing unit 74 identifies a denomination, a transport state, and the like, of the banknote 100 present on the transport path 60 by comparing data obtained by using the recognition sensor unit 20 from the banknote 100 that is being transported on the transport path 60 with the data for recognition 82. Similarly, the recognition processing unit 74 recognizes a denomination of the transported banknote 100 by comparing data obtained by using the spectroscopy unit 30 from the transported banknote 100 with the data for recognition 82. Moreover, similarly, the recognition processing unit 74 also performs recognition of authenticity, fitness, and the like, of the banknote 100 by using the data for recognition 82.

The optical spectrum measurement condition 81 is stored as a measurement condition for acquiring the optical spectrum from a predetermined partial area on the banknote 100. As the optical spectrum measurement condition 81, information for identifying one or more of the light sources among the light sources 601a to 608a and 601b to 608b included in the light source unit 31 that shall emit a light on a partial area, information for identifying a timing to turn on the identified light source based on the transport position of the banknote 100 on the transport path 60, and information for identifying a timing to turn off the light source that was turned on, and the like, are stored in a related manner. The optical spectrum measurement condition 81 includes, in addition, a current value to be used when turning on the light source, information for identifying a timing at which the data acquisition unit 73 shall start acquisition of a signal relating to the optical spectrum from the sensor unit 34, information for identifying a timing to stop the acquisition of the signal from the sensor unit 34, information for identifying a gain adjustment quantity for the signal acquired from the sensor unit 34, and the like. In the recognition unit 1, when a denomination, a face/back direction, a portrait direction, of the banknote 100 that is transported on the transport path 60 can be identified, a control method of the light source unit 31 by the light-source control unit 72 and an acquisition method of data from the sensor unit 34 by the data acquisition unit 73 can be determined by referring to the optical spectrum measurement condition 81, and the optical spectrum can be acquired from the banknote 100 present on the transport path 60.

Specifically, the recognition processing unit 74, at first, acquires data by using the recognition sensor unit 20 that is arranged upstream from the spectroscopy unit 30 in the transport direction and identifies a type, such as a denomination, a version, and the like, of the banknote 100 from the acquired data, and identifies a transport state of the banknote 100. The identification of the transport state of the banknote 100 includes determining whether the banknote 100 is being transported with a face side up or a back side up, whether a front side of the banknote 100 in the transport direction is a portrait normal direction or a portrait reverse direction, and the like. Then, by referring to the optical spectrum measurement condition 81 based on the information relating to the type and the transport state of the banknote 100 identified by the recognition processing unit 74, the light-source control unit 72 recognizes a type of the light excited on the banknote 100, a partial area on the banknote 100 from which the light is excited, an emission type and an emission method for exciting the light in this partial area, a positional relationship between this partial area and the light sources 601a to 608a and 601b to 608b of the light source unit 31, and the like. Similarly, the data acquisition unit 73 recognizes, based on the optical spectrum measurement condition 81, a type of the light excited on the banknote 100, a partial area on the banknote 100 from which the light is excited, a measurement method of the light excited from this partial area, a positional relationship between this partial area and the light receiving surfaces 501 to 516 of the reading unit 32, and the like. In this manner, a method of excitation of the light on the banknote 100 and a method of measurement of the excited light are set.

Once the method of excitation of the light on the banknote 100 and the method of measurement of the excited light on the banknote 100 are set, the light-source control unit 72 controls the light source unit 31 and emits the light at the timing when the banknote 100 that is being transported on the transport path 60 passes the reading area of the spectroscopy unit 30, and the data acquisition unit 73 acquires data relating to the optical spectrum from the sensor unit 34. From thus-obtained optical spectrum, it can be determined whether a predetermined light was excited by emission of a predetermined light on a predetermined partial area on the banknote 100. Accordingly, a recognition precision of the banknote 100 can be increased by using the data obtained in the data acquisition unit 73 for the recognition processing of the banknote 100 performed by the recognition processing unit 74.

In the recognition unit 1, by making a setting based on the optical spectrum measurement condition 81, an optical spectrum of the entire surface of the banknote 100 can be measured, or an optical spectrum can be acquired from only one or more of the partial areas. Moreover, various luminous phenomena can be measured by changing the type of the light to be emitted on the banknote 100. Furthermore, the optical spectrum of the phosphorescence can be acquired in addition to the fluorescence by changing an acquisition timing of the optical spectrum. A concrete acquisition method of the optical spectrum is explained below by using an example in which the light source unit 31 includes a first light source unit 31a that emits an ultraviolet light (hereinafter, "UV light") and a second light source unit 31b that emits an infrared light (hereinafter, "IR light").

The first light source unit 31a and the second light source unit 31b are realized by the light sources 601a to 608a and 601b to 608b. Specifically, each of the light sources 601a to 608a and 601b to 608b can emit one or both of the UV light and the IR light. When a control for the first light source unit 31a is provided so as to emit the UV light, the light sources 601a to 608a and 601b to 608b emit the UV light. Moreover, when a control for the second light source unit 31b is provided so as to emit the IR light, the light sources 601a to 608a and 601b to 608b emit the IR light.

FIGS. 6A to 6D are views for explaining the method of acquiring the data relating to the optical characteristics from the entire surface of the banknote 100 by controlling the operation of the spectroscopy unit 30. FIG. 6A shows channels formed by the light receiving surfaces 501 to 516 and the light sources 601a to 608a and 601b to 608b of the spectroscopy unit 30. FIG. 6B shows blocks 701 to 740 obtained by dividing the entire surface of the banknote 100 into a plurality of partial areas corresponding to each of the channels shown in FIG. 6A. FIG. 6C depicts the optical spectrum measurement condition 81 used to control the light source unit 31 and the sensor unit 34 when acquiring the data from all the blocks 701 to 740 shown in FIG. 6B. FIG. 6D shows a control method of the first light source unit 31a, the second light source unit 31b, and the sensor unit 34 based on the optical spectrum measurement condition 81 shown in FIG. 6C.

As shown in FIG. 6A, the light receiving surface 501, the light receiving surface 502, the light source 601a, and the light source 601b are controlled as one set (one channel) in the spectroscopy unit 30. By similar channel setting, the spectroscopy unit 30 is divided into eight channels, channels 1 to 8 (Ch1 to Ch8 in figure), by combining two light receiving surfaces and two light sources.

In FIG. 6B, the upper direction in the drawing sheet is the transport direction of the banknote 100. For example, the light sources 601a and 601b of the channel 1 are turned on in the light source unit 31 at a timing at which the block 701 shown in FIG. 6B overlaps a reading area, which is read by the reading unit 32, right below the spectroscopy unit 30. The optical spectrum of the block 701 can be acquired with the sensor unit 34 by receiving a reflected light from the banknote 100 in the light receiving surfaces 501 and 502 of the reading unit 32.

The sensor unit 34 acquires, by using a prism and the like, the optical spectrum from the light received in all the light receiving surfaces 501 to 516. The optical spectrum of the block 701 can be acquired by emitting light to the block 701 by turning on only the light sources 601a and 601b of the channel 1 and receiving the reflected light from the block 701 in the light receiving surfaces 501 and 502. That is, in an environment where there is no noise light and only the light from the light source is emitted on the banknote 100, the lights are emitted from the light sources to the partial area targeted for the acquisition of the optical spectrum on the banknote 100, and the optical spectrum can be acquired by reading the light that is excited in this partial area.

The transport of the banknote 100 on the transport path 60 is continued while the light is being emitted in the block 701 and data is being acquired. Therefore, when successively acquiring data from the block 702 after having acquired the data from the block 701, the position of the block 702 will be shifted from a position of the block 701 to an opposite direction of the transport direction (lower direction in the drawing sheet). For example, when the transport speed of the banknote 100 is 2000 mm/s and the time taken to acquire the data of the block 701 is 500 μs, the amount of shift between the block 701 and the block 702 along the transport direction will be 1 mm. As a result, in one line of the blocks 701 to 708, there will occur a shift of 8 mm along the transport direction. By setting the blocks 701 to 740 on the banknote 100 as shown in FIG. 6B, the optical spectrum can be acquired from each of the blocks 701 to 740 for the entire surface of the banknote 100 that is being transported at a high speed.

FIG. 6C depicts the optical spectrum measurement condition 81 used to acquire the optical spectrum from the blocks 701 to 740 from the entire surface of the banknote 100, namely sequentially all the blocks 701 to 740 shown in FIG. 6B. The optical spectrum measurement condition 81 includes the following items: "No." indicating the order of measurement, "banknote position" indicating a position of the banknote 100 in millimeters on the transport path 60, "sensor" in which is set the measurement method for the sensor unit 34, "first light source" in which is set the control method for the first light source unit 31a that emits the UV light, and "second light source" in which is set the control method for the second light source unit 31b that emits the IR light.

The optical spectrum measurement condition 81 shown in FIG. 6C is an example of emitting the UV light on the entire surface of the banknote 100 and measuring the fluorescence. Specifically, the setting contents correspond to a situation in which the fluorescence excited on the banknote 100 is measured while the UV light is being emitted by using only the first light source unit 31a.

In the item "banknote position" contained in the optical spectrum measurement condition 81, the position of the banknote 100 on the transport path 60 when the spectroscopy unit 30 starts performing the measurement of the block 701 shown in FIG. 6B is set to 0 mm. The banknote position of the banknote 100 after 500 μs from completion of the measurement of the block 701 will be 1 mm, and the banknote position of the banknote 100 after 500 μs thereafter will be 2 mm.

Moreover, each of the items "measurement start" below the item of "sensor" of the optical spectrum measurement condition 81, "lighting start" below the item of "first light source", and "lighting start" below the item of "second light source" indicates that, under the condition where the timing at which the banknote 100 reaches that particular banknote position is set to 0 (zero), after how many seconds the measurement or the lighting is to be started.

For example, the item of "sensor" of No. 0 (zero) shown in FIG. 6C shows that the measurement by the sensor unit 34 is started at a timing (0 μs) at which the banknote position is 0 mm. The measurement of the gain is 1, and the measurement is completed after elapse of 500 μs. Moreover, the item of "first light source" of No. 0 (zero) shows that the emission of the UV light is started by turning on the light sources 601a and 601b of the channel 1 of the first light source unit 31a at a timing (0 μs) at which the banknote 100 reached the banknote position of 0 mm. The current value of the emission is 10 mA, and the light sources 601a and 601b are turned off after elapse of 500 μs from the start of the emission. When the measurement of No. 0 is completed in the block 701 with the banknote 100 being transported at 2000 mm/s, the banknote position will be 1 mm. Then, the measurement of No. 1 is started at the banknote position of 1 mm and the measurement of the block 702 is performed. In the measurement of No. 1, the light sources 602a and 602b of the channel 2 of the first light source unit 31a are turned on at a current value of 10 mA and the UV light is emitted for a period of 500 μs, and the measurement is performed by the sensor unit 34 during the period of 500 μs. That is, the optical spectrum measurement condition 81 shown in FIG. 6C corresponds to the settings for performing alternate lighting control in which the measurement is performed while sequentially turning on and off the light sources of the channels 1 to 8 of the first light source unit 31a.

FIG. 6D shows a timing chart of a control method of the first light source unit 31a, the second light source unit 31b, and the sensor unit 34 based on the optical spectrum measurement condition 81 shown in FIG. 6C. In all timing charts in the present embodiment, including the timing charts shown in FIG. 6D, time passes as one goes towards right, and the elapsed time is shown as the banknote position at the top of the timing chart. The value of the banknote position of the timing chart corresponds to the banknote position in the optical spectrum measurement condition 81, and a difference of 1 mm in this value corresponds to a period of 500 μs. The light sources that are turned on to acquire the optical spectrum are shown by charts for the first light source unit 31a and the second light source unit 31b, and charts for each of the channels 1 to 8 (Ch1 to Ch8 in figure). For example, in the example shown in FIG. 6D, only the first light source unit 31a and the channel 1 are in on-states between the banknote positions 0 mm and 1 mm. This means that only the light sources 601a and 601b of the channel 1 of the first light source unit 31a are turned on and the other light sources are not turned on. Moreover, in the chart of the sensor unit 34, an off-state shows a state in which no measurement is performed, and an on-state shows a state in which the measurement of the optical spectrum is performed by receiving the light from the light receiving surfaces 501 to 516 of the reading unit 32. In the optical spectrum measurement condition 81 shown in FIG. 6C, as shown in FIG. 6D, after performing the measurement of the optical spectrum by emitting the UV light in the channel 1 between the banknote positions 0 mm and 1 mm, the measurement of the optical spectrum is performed by emitting the UV light in the channel 2 between the banknote positions 1 mm and 2 mm. Similar operation is continued and the measurement of the optical spectrum is performed by emitting the UV light in the channels 1 to 8 of the first light source unit 31a one by one.

By performing based on the optical spectrum measurement condition 81 the alternate lighting control, in which the light sources of each of the channels 1 to 8 are turned on/off sequentially, between the banknote positions 0 mm and 8 mm, the data of a first line of the blocks 701 to 708 shown in FIG. 6B can be acquired by the sensor unit 34. Then, when the banknote position reaches 8 mm, by again turning on/off the light sources of each of the channels 1 to 8 one by one, the data of a second line of the blocks 709 to 716 can be acquired by the sensor unit 34. In this manner, by acquiring the optical spectrum from the light received in the light receiving surfaces 501 to 516 by controlling the on timing and the off timing of the light sources of each of the channels 1 to 8, the optical spectrum can be acquired from the blocks 701 to 740 that constitute the entire surface of the banknote 100.

In this manner, in the recognition unit 1, the optical spectrum can be acquired from the entire surface of the banknote 100 by previously preparing the settings, i.e., the optical spectrum measurement condition 81, for acquiring the optical spectrum from each of the blocks 701 to 740 one by one.

A concrete example of acquiring the optical spectrum of the banknote 100 by the measurement method shown in FIGS. 6A to 6D is explained below. FIGS. 7A to 7E are views indicating a method of acquiring the optical spectrum from the partial areas from which the light is excited on the banknote 100 by measuring an entire surface of the banknote 100.

Figure 7A:
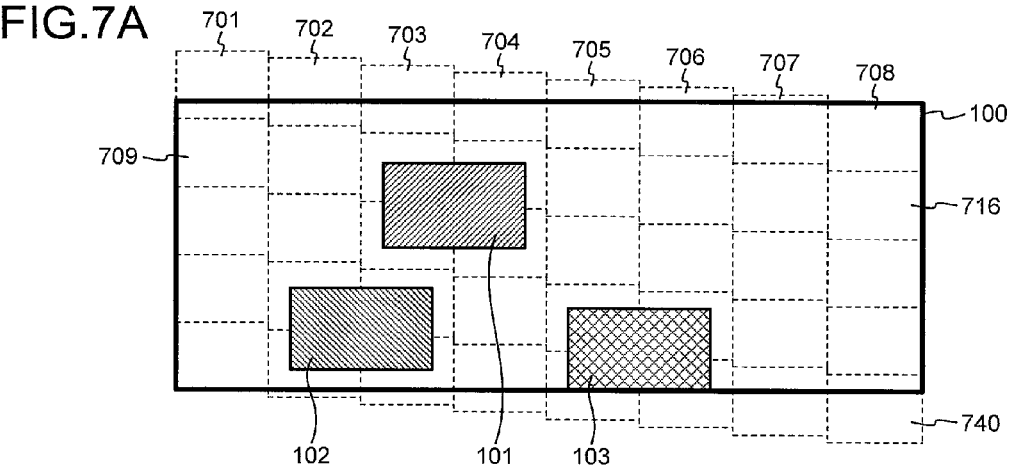
FIGS. 7A, 7B, 7C, 7D, and 7E are views for explaining a method of acquiring data relating to optical characteristics from partial areas on a banknote by measuring an entire surface of the banknote.

FIG. 7A shows an example of the banknote 100 in which the fluorescence is excited in three partial areas 101 to 103 when irradiated with the UV light. As shown in FIG. 7A, each of the partial areas 101 to 103 is contained in four blocks set on the banknote 100. Therefore, when measurement is performed in the entire surface of the banknote with the method shown in FIGS. 6A to 6D, the optical spectrum of the fluorescence excited in each of the partial areas 101 to 103 is acquired in 12 blocks corresponding to the three partial areas 101 to 103.

Figure 7B:
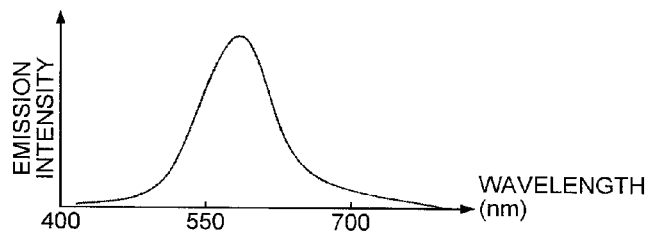
Figure 7C:
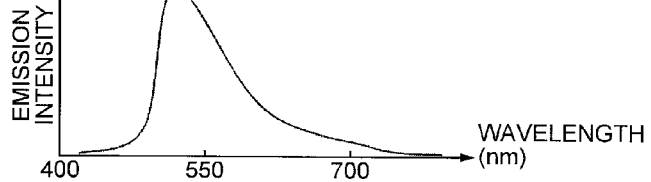
Figure 7D:
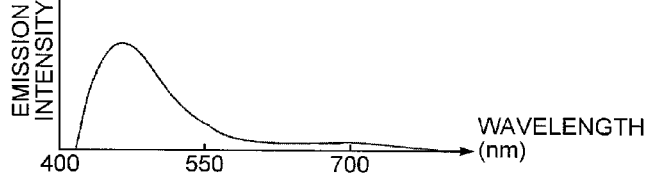

FIGS. 7B to 7D respectively show the optical spectrum acquired in the blocks corresponding to each of the partial areas 101 to 103. As shown in FIGS. 7B to 7D, the optical spectrums having different features, such as a peak wavelength, a peak level, a signal waveform, and the like, are acquired in the three partial areas 101 to 103. The features of the acquired optical spectrums can be used for performing the recognition of the denomination, the authenticity, and the like of the banknote 100.

In the recognition unit 1, apart from performing the recognition of the banknote 100 based on the features, such as the peak wavelength, the peak level, the signal waveform of the optical spectrum that appear in the optical spectrum, the recognition of the banknote 100 can be performed based on the banknote image generated from the optical spectrum. The generation of the banknote image is performed by the data acquisition unit 73, and the recognition of the banknote 100 is performed by the recognition processing unit 74.

Figure 7E:
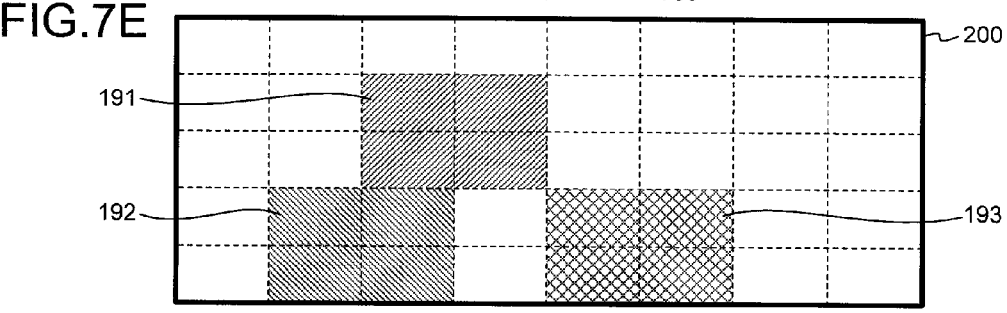

FIG. 7E is a schematic diagram of a banknote image 200 of the banknote 100 shown in FIG. 7A. The banknote image is generated based on the optical spectrums shown in FIGS. 7B to 7D. The banknote image 200 is constituted by 40 blocks. The blocks are obtained by dividing the entire surface of the banknote into 40 blocks corresponding to the blocks 701 to 740 used for acquiring the optical spectrums.

In FIG. 7E, partial areas 191 to 193 corresponding to the partial areas 101 to 103 from which the fluorescence is excited are shown in different patterns; however, in an actual image, each of the areas 191 to 193 are colored images with different colors and the lightness. Specifically, by using a method set previously, the image of each of the blocks of the banknote image 200 is generated from the optical spectrum obtained in each of the blocks 701 to 740 set on the banknote 100. For example, if the optical spectrum acquired in a block of the banknote 100 has a peak only in a red wavelength band, the image of this block will be made a red image. If the optical spectrum acquired in a block of the banknote 100 has a peak only in a green wavelength band, the image of this block will be made a green image. If the optical spectrum acquired in a block of the banknote 100 has peaks in both the red and green wavelength bands, the image of this block will be made an image of a color obtained by mixing red and green depending on the peak ratio. Moreover, for example, the lightness of the image is changed depending on the peak level. If the optical spectrum of a block has no characteristic waveform, the image of this block is displayed in a background color. The background color is not particularly limited; however, for convenience in showing in figures, the background color is shown as white in the present embodiment.

For example, corresponding to the four blocks 711, 712, 719, 720 that include the partial area 101 of the banknote 100 shown in FIG. 7A, the partial area 191 in the banknote image 200 is constituted by four blocks as shown in FIG. 7E. As shown in FIG. 7B, because an optical spectrum having a peak in a yellow wavelength band is obtained from the partial area 101 of the banknote 100, the partial area 191 of the banknote image 200 is a yellow image. Moreover, as shown in FIG. 7C, because an optical spectrum having a peak in a green wavelength band is obtained from the partial area 102 on the banknote 100, the partial area 192 of the banknote image 200 corresponding to the partial area 102 is a green image. Moreover, as shown in FIG. 7D, because an optical spectrum having a peak in a blue wavelength band is obtained from the partial area 103 on the banknote 100, the partial area 193 of the banknote image 200 corresponding to the partial area 103 is a blue image. In this manner, corresponding to the partial areas 101 to 103 from which the fluorescence emissions are excited on the banknote 100, the corresponding partial areas 191 to 193 of the banknote image 200 are displayed as colored images. On the other hand, the blocks in which emission of light was not observed when the entire surface of the banknote 100 is measured are displayed in a white background color.

In this manner, in the banknote image 200, the region corresponding to the block on the banknote 100 in which the fluorescence is excited is displayed as an image that matches with the optical spectrum of the fluorescence excited in that block. Because the position of the block in which the emission of fluorescence is observed, the optical spectrum obtained in each block, and the like, are different depending on the type of the banknote 100, a denomination, authenticity, and the like, of the banknote 100 can be recognized based on the banknote image 200.

For example, by previously storing banknote images, each of which is generated based on the optical spectrum of the banknote 100 per denomination, as the data for recognition 82 in the memory 80, a denomination and the like of the banknote 100 can be determined based on a correlation between the stored banknote images and the banknote image 200 generated from the optical spectrum by the data acquisition unit 73.

In the recognition unit 1, apart from acquiring the optical spectrum of the entire surface of the banknote 100 as shown in FIGS. 6A to 6D, it is possible to acquire an optical spectrum from only a predetermined partial area on the banknote 100. A method to acquire the data relating to the optical characteristics only from partial areas 111 to 113 on the banknote 100 is explained below by taking the banknote 100 shown in FIG. 8A as an example.

FIGS. 8A to 8D are views of an example of the banknote 100 on which emission of light is observed in the three partial areas 111 to 113. FIG. 8A shows the three partial areas 111 to 113 in which emission of light is observed on the banknote 100, and FIGS. 8B to 8D show optical spectrums of the light measured in each of the partial areas 111 to 113. Specifically, as shown in FIG. 8B, when the IR light is emitted in the partial area 111, an optical spectrum of a reflected light is acquired from the partial area 111. Moreover, as shown in FIG. 8C, when the UV light is emitted in the partial area 112, an optical spectrum of fluorescence is acquired from the partial area 112. Moreover, as shown in FIG. 8D, when the UV light is emitted in the partial area 113, an optical spectrum of fluorescence of a wavelength band of 700 nm or less is acquired from the partial area 113, and when the IR light is emitted in the partial area 113, an optical spectrum of a reflected light of a wavelength band of more than 700 nm is acquired from the partial area 113. To acquire the optical spectrum of each of the partial areas 111 to 113 by the spectroscopy unit 30 from the banknote 100 having such optical characteristics, the optical spectrum measurement condition 81 is set as shown in FIGS. 9A to 9C.

Figure 9A:
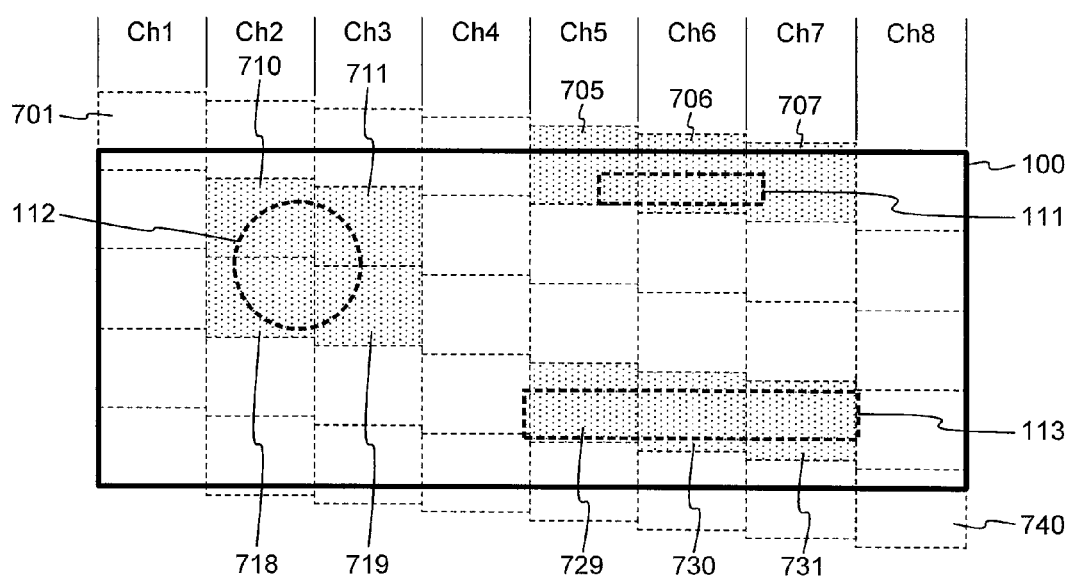
Figure 9C:
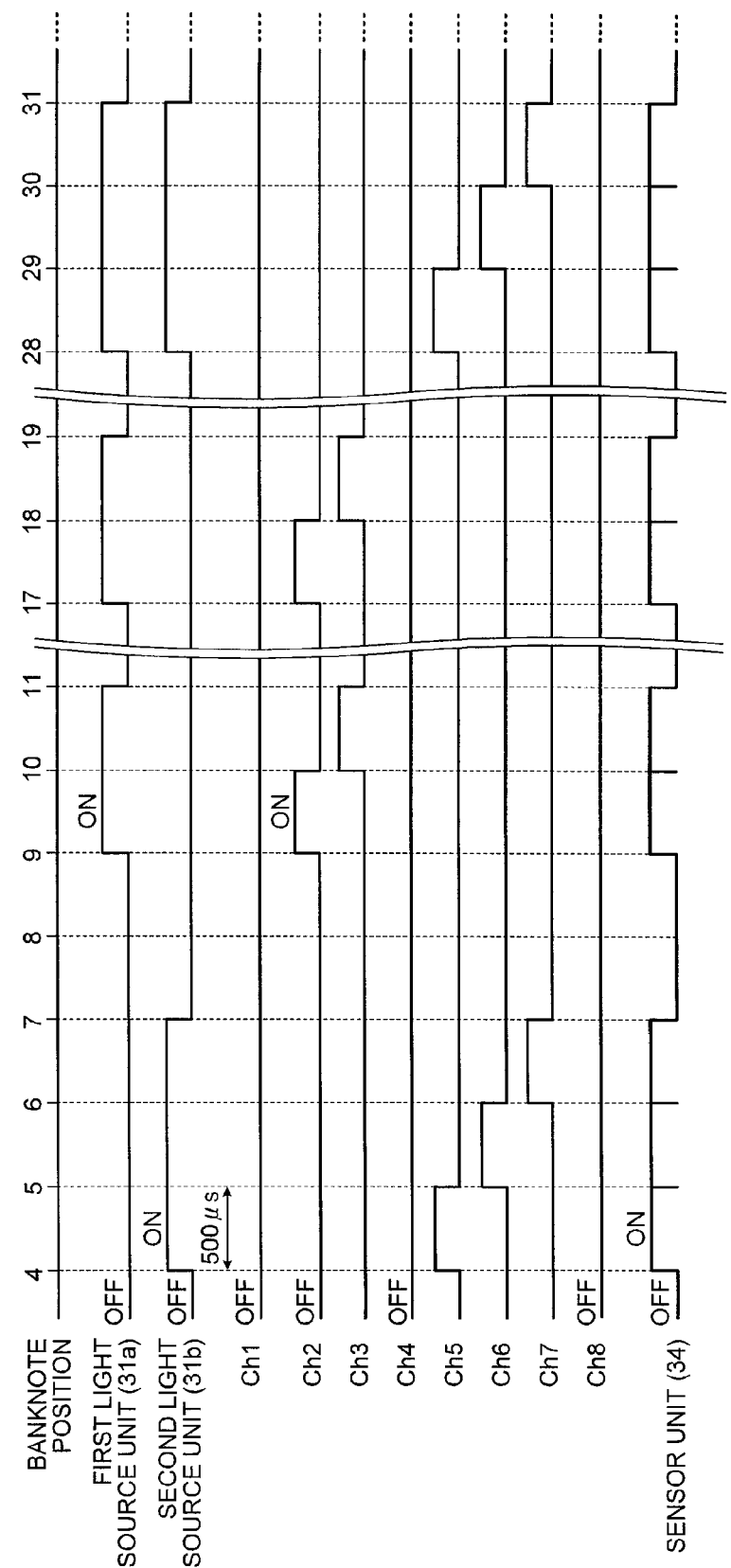

FIGS. 9A to 9C are views for explaining the optical spectrum measurement condition 81 set for the banknote 100 shown in FIG. 8A. FIG. 9A shows positional relationships among the partial areas 111 to 113 on the banknote 100 and the blocks 701 to 740 set on the banknote 100, FIG. 9B shows setting contents of the optical spectrum measurement condition 81, FIG. 9C shows a timing chart of operations performed by the first light source unit 31a, the second light source unit 31b, and the sensor unit 34 when acquiring optical spectrums based on the optical spectrum measurement condition 81.

In the example shown in FIG. 9A, the same blocks 701 to 740 shown in FIG. 6B are used; however, the block configuration to be used when acquiring the optical spectrum is not limited to that shown in FIG. 6B. For example, the partial area 111 shown in FIG. 9A is included in four blocks; however, the blocks can be set so that the partial area 111 is included in three or less blocks, or the blocks can be set so that the partial area 111 is included in five or more blocks. By setting a banknote position, a lighting start timing and a lighting duration of the first light source unit 31a and the second light source unit 31b, and a measurement start timing and a measurement duration of the sensor unit 34 in the optical spectrum measurement condition 81 shown in FIG. 9B, blocks of desired sizes can be set at desired positions on the banknote 100 and measurement of the optical spectrum can be performed in those blocks; however, an example in which the measurement of the optical spectrum is performed by using the block configuration shown in FIG. 6B is explained in the present embodiment.

As shown in FIG. 9A, if emission of light is observed only in the predetermined partial areas 111 to 113 on the banknote 100, data can be acquired in the recognition unit 1 from only these partial areas 111 to 113. Specifically, as shown in FIG. 9A, optical spectrums are measured only in the blocks 705 to 707 corresponding to the partial area 111, in the blocks 710, 711, 718, 719 corresponding to the partial area 112, and in the blocks 729 to 731 corresponding to the partial area 113.

For example, in a situation in which only the banknote 100 shown in FIG. 9A is handled in the banknote handling apparatus 2, or in a situation in which the recognition processing unit 74 recognized, based on the data obtained by the recognition sensor unit 20, that the denomination of the banknote 100 that is being transported on the transport path 60 is the same as that of the banknote 100 shown in FIG. 9A, an operation to acquire the optical spectrums only from the partial areas 111 to 113 as shown in FIG. 9C is performed by using the optical spectrum measurement condition 81 shown in FIG. 9B.

As shown in FIGS. 9B and 9C, acquisition of the optical spectrum is not performed even if the position of the banknote 100 reaches the banknote position 0 mm, and when the banknote 100 that is being transported at the transport speed of 2000 mm/s is transported further and the banknote position reaches 4 mm, the measurement of No. 0 (zero) is started at this timing. In the measurement of No. 0, the timing at which the banknote 100 reaches the banknote position 4 mm is set to 0 μs, and during a period of 500 μs from this timing, the light sources 605a and 605b of the channel 5 of the second light source unit 31b are turned on at a current value of 10 mA and the IR light is emitted. Then, during this period of 500 μs during which the IR light is emitted from the second light source unit 31b, the sensor unit 34 acquires an optical spectrum to acquire an optical spectrum of the light excited in the block 705. Subsequently, in the measurements shown in No. 1 and No. 2 of the optical spectrum measurement condition 81, similarly, an optical spectrum of the light excited in the blocks 706 and 707 is acquired by emitting the IR light from the second light source unit 31b. In this manner, by performing the measurements shown in No. 0 to No. 2, the optical spectrums of the light excited when the IR light is emitted can be acquired from the blocks 705 to 707 corresponding to the partial area 111.

After completion of the measurement of the optical spectrum in the block 707 between the banknote positions 6 mm and 7 mm, no light source is turned on and no optical spectrum is acquired until the banknote position reaches 9 mm. Then, when the banknote position of the banknote 100 reaches 9 mm, the measurement of the optical spectrum is started again. As shown in FIGS. 9B and 9C, the measurements shown in No. 3 to No. 6 of the optical spectrum measurement condition 81 are performed, and the optical spectrums are acquired for the blocks 710, 711, 718, 719 corresponding to the partial area 112. Specifically, in the measurement of No. 3, the timing at which the banknote 100 reaches the banknote position 9 mm is set to 0 μs, and during a period of 500 μs from this timing, the light sources 602a and 602b of the channel 2 of the first light source unit 31a are turned on at a current value of 10 mA and the UV light is emitted. Then, during the period of 500 μs during which the UV light is emitted, the sensor unit 34 acquires an optical spectrum to acquire an optical spectrum of the light excited in the block 710. Subsequently, in the measurement shown in No. 4 of the optical spectrum measurement condition 81, similarly, an optical spectrum of the light excited in the block 711 is acquired by emitting the UV light from the first light source unit 31a. After having acquired the optical spectrum in the block 711, the measurement is stopped. Then, the measurement is started again when the banknote position reaches 17 mm, and the optical spectrums are acquired in the blocks 718 and 719 by performing the measurements shown in No. 5 and No. 6 shown in the optical spectrum measurement condition 81. In this way, the optical spectrums can be acquired in the blocks 710, 711, 718, 719 corresponding to the partial area 112 by performing the measurements of No. 3 to No. 6.

After completion of the measurement of the optical spectrum in the block 719 between the banknote positions 18 mm and 19 mm, the measurement is stopped, and the measurement is started again when the banknote position reaches 28 mm. Specifically, in the measurements of No. 7 to No. 9, the UV light is emitted from the channels 5 to 7 of the first light source unit 31a sequentially and the IR light is also emitted from the channels 5 to 7 of the second light source unit 31b sequentially. Accordingly, both the optical spectrums for the UV light and the optical spectrums for the IR light are acquired in the blocks 729 to 731 corresponding to the partial area 113.

In this manner, when the partial area from which the optical spectrum is to be acquired on the banknote 100 is previously known, the processing load can be reduced by acquiring the optical spectrum only from this partial area. For example, in the example shown in FIGS. 9A to 9C, by measuring the optical spectrums only in 10 blocks among the 40 blocks 701 to 740 that constitute the banknote 100, the optical spectrums can be acquired in all the partial areas 111 to 113 in which the emission of light is observed on the banknote 100.

In this way, the optical spectrum shown in FIG. 8B is acquired in the blocks 705 to 707 corresponding to the partial area 111, the optical spectrum shown in FIG. 8C is acquired in the blocks 710, 711, 718, 719 corresponding to the partial area 112, and the optical spectrum shown in FIG. 8D is acquired in the blocks 729 to 731 corresponding to the partial area 113.

Figure 10A:
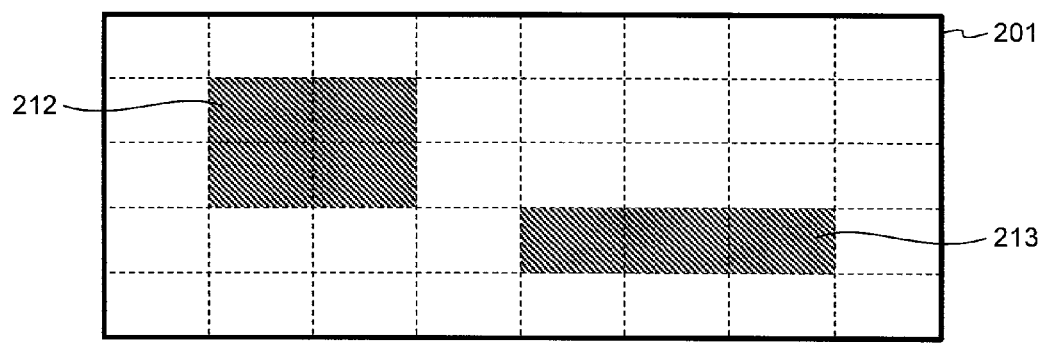
FIGS. 10A and 10B are schematic diagrams of banknote images of the banknote shown in FIG. 8A generated based on optical spectrums.
Figure 10B:
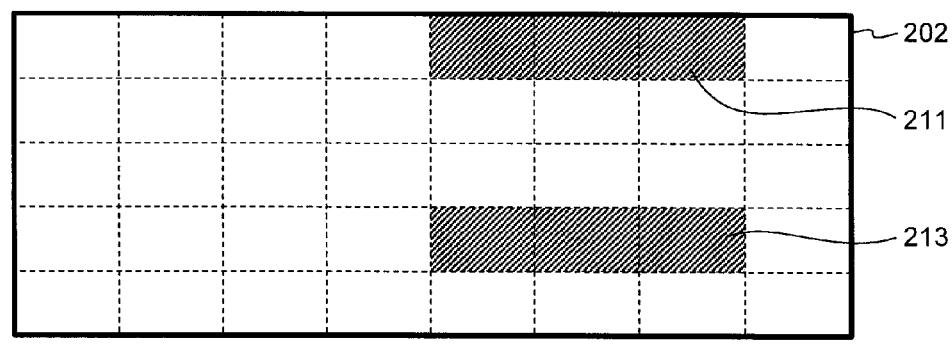

FIGS. 10A and 10B are schematic diagrams of banknote images 201 and 202 generated from the optical spectrums of the partial areas 111 to 113. In the same manner as in FIG. 7E, in the actual banknote images 201 and 202, each of areas 211 to 213 are colored images depending on the optical spectrums; however, in FIGS. 10A and 10B these images are shown schematically with different patterns.

FIG. 10A shows the banknote image 201 generated from the optical spectrum that is obtained by emitting the UV light, and FIG. 10B shows the banknote image 202 generated from the optical spectrum that is obtained by emitting the IR light. In this manner, in the recognition unit 1, it is possible to generate separate banknote images 201 and 202 depending on the type of the light emitted from the light source unit 31.

As shown in FIGS. 8A to 8D, because the optical spectrums of the fluorescence emissions are acquired in the partial areas 112 and 113 when the UV light is emitted, as shown in FIG. 10A, the partial areas 212 and 213 on the banknote image 201 corresponding to the partial areas 112 and 113 on the banknote 100 are images of colors that depend on the optical spectrums. Similarly, because the optical spectrums of the reflected lights are acquired in the partial areas 111 and 113 when the IR light is emitted, as shown in FIG. 10B, the partial areas 211 and 213 on the banknote image 202 corresponding to the partial areas 111 and 113 on the banknote 100 are images of colors that depend on the optical spectrums.

If the banknote image acquired when the UV light is emitted on the banknote 100 shown in FIG. 8A, and the banknote image acquired when the IR light is emitted on the banknote 100 shown in FIG. 8A are previously stored in the memory 80 as the data for recognition 82, it can be determined whether the banknote 100 that is being transported is the banknote 100 shown in FIG. 8A or not, based on a correlation between these previously stored images and the banknote images 201 and 202 that are generated from the optical spectrums acquired from the banknote 100 that is being transported on the transport path 60.

In the recognition unit 1, the optical spectrums of the phosphorescence can be acquired in addition to the fluorescence. A method to acquire the data relating to the optical characteristics of the banknote 100 shown in FIG. 11A on which emission of fluorescence and emission of phosphorescence are observed is explained below as an example.

Figure 11A:
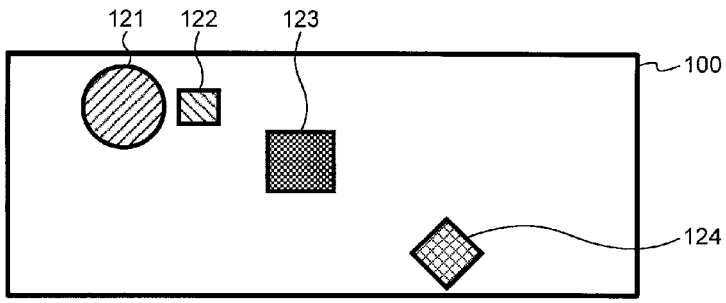
Figure 11A:
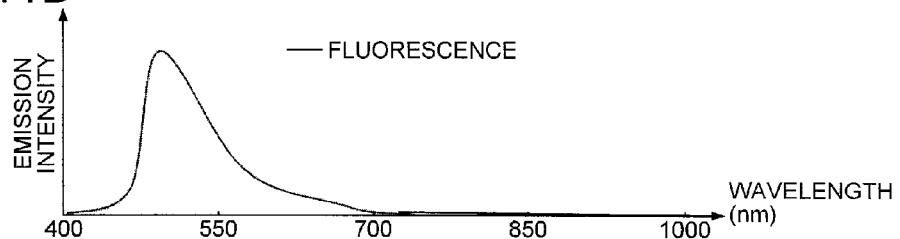
Figure 11A:
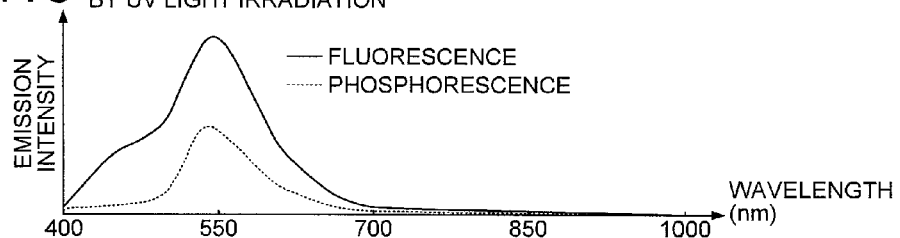
Figure 11A:
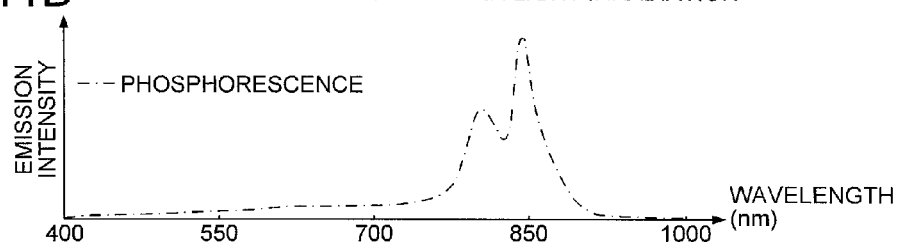
Figure 11A:
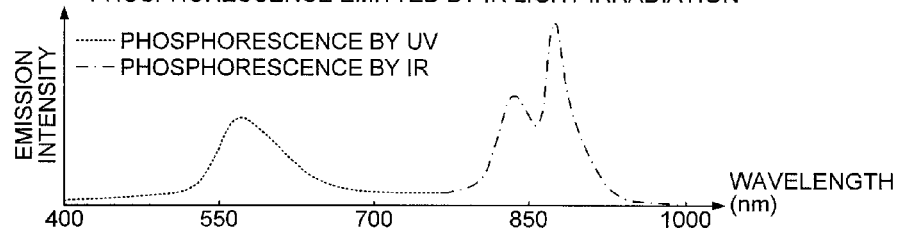

FIGS. 11A to 11E are views of an example of the banknote 100 from which the emission of light is observed in four partial areas 121 to 124. FIG. 11A shows the four partial areas 121 to 124 from which the emission of light is observed on the banknote 100, and FIGS. 11B to 11E show optical spectrums of the light measured in each of the partial areas 121 to 124. Specifically, as shown in FIG. 11B, when the UV light is emitted in the partial area 121, an optical spectrum of the fluorescence is acquired from the partial area 121. Moreover, as shown in FIG. 11C, when the UV light is emitted in the partial area 122, optical spectrums of the fluorescence and the phosphorescence are acquired from the partial area 122. As shown in FIG. 11D, when the IR light is emitted in the partial area 123, an optical spectrum of the phosphorescence is acquired from the partial area 123.

Moreover, as shown in FIG. 11E, when the UV light is emitted in the partial area 124, an optical spectrum of the phosphorescence of a wavelength band of 700 nm or less is acquired from the partial area 124, and when the IR light is emitted in the partial area 124, an optical spectrum of the phosphorescence of a wavelength band of more than 700 nm is acquired from the partial area 124. To acquire the optical spectrum of each of the partial areas 121 to 124 by the spectroscopy unit 30 from the banknote 100 having such optical characteristics, the optical spectrum measurement condition 81 is set as shown in FIGS. 12A to 12C.

The positions and the sizes of the blocks can be set based on the partial areas 121 to 124 shown in FIG. 11A; however, an example in which the measurement of the optical spectrum is performed by using the block configuration shown in FIG. 6B is explained in the present embodiment. It is not necessary to measure the optical spectrum right above the partial area that emits the light. Therefore, as shown in FIG. 12A, even if a part of the partial areas 121, 123, 124 in which the light is excited on the banknote 100 are out of the area of the blocks 710, 720, 730 to be measured, the optical spectrum of the light excited in each of the partial areas 121, 123, 124 can be measured from the blocks 710, 720, 730. Moreover, conversely, even if the partial area 122 completely falls within the block 711 whereby the partial area 122 is only a part of the block 711, the optical spectrum of the light excited in the partial area 122 can be measured from the block 711.

Figure 12A:
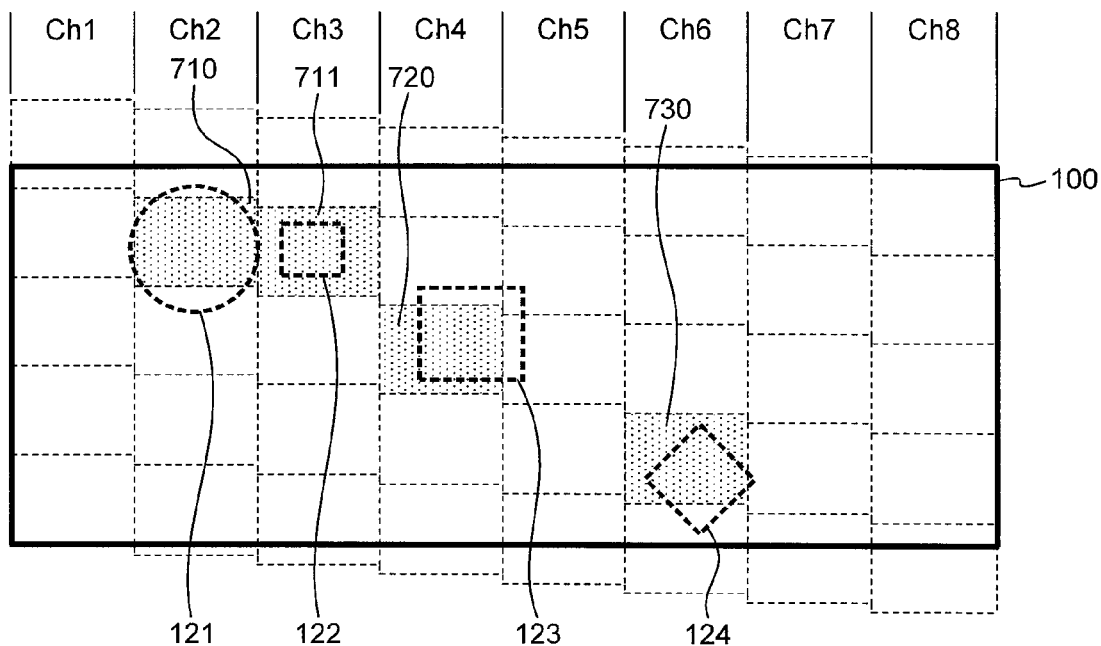

FIGS. 12A to 12C are views for explaining the optical spectrum measurement condition 81 set for the banknote 100 shown in FIG. 11A. FIG. 12A shows positional relationships among the partial areas 121 to 124 on the banknote 100 and the blocks 701 to 740 set on the banknote 100, FIG. 12B shows setting contents of the optical spectrum measurement condition 81, FIG. 12C shows a timing chart of operations performed by the first light source unit 31a, the second light source unit 31b, and the sensor unit 34 when acquiring an optical spectrum based on the optical spectrum measurement condition 81.

As shown in FIG. 12A, if emission of light is observed only in the predetermined partial areas 121 to 124 on the banknote 100, data can be acquired from only these partial areas 121 to 124. Specifically, as shown in FIG. 12A, optical spectrums are measured only in the block 710 corresponding to the partial area 121, the block 711 corresponding to the partial area 122, the block 720 corresponding to the partial area 123, and the block 730 corresponding to the partial area 124.

For example, in a situation in which only the banknote 100 shown in FIG. 12A is handled in the banknote handling apparatus 2, or in a situation in which the recognition processing unit 74 recognized, based on the data obtained by the recognition sensor unit 20, that the denomination of the banknote 100 that is being transported on the transport path 60 is the same as that of the banknote 100 shown in FIG. 12A, an operation to acquire the optical spectrums only from the partial areas 121 to 124 as shown in FIG. 12C is performed by using the optical spectrum measurement condition 81 shown in FIG. 12B.

As shown in FIGS. 12B and 12C, acquisition of the optical spectrum is not performed even if the position of the banknote 100 reaches the banknote position 0 mm, and when the banknote 100 that is being transported at the transport speed of 2000 mm/s is transported further and the banknote position reaches 9 mm, the measurement of No. 0 (zero) is started at this timing. In the measurement of No. 0, the timing at which the banknote 100 reaches the banknote position 9 mm is set to 0 μs, and during a period of 500 μs from this timing, the light sources 602*a* and 602*b* of the channel 2 of the first light source unit 31*a* are turned on at a current value of 10 mA and the UV light is emitted. Then, during this period of 500 μs during which the UV light is emitted from the first light source unit 31*a*, the sensor unit 34 acquires an optical spectrum to acquire an optical spectrum of the light excited in the block 710. Subsequently, in the measurements shown in No. 1 and No. 2 of the optical spectrum measurement condition 81, optical spectrums of the fluorescence and the phosphorescence excited in the block 711 are acquired by emitting the UV light from the light sources 603*a* and 603*b* of the channel 3 of the first light source unit 31*a*.

Specifically, in the measurement No. 1, during a period of 500 μs between the banknote positions 10 mm and 11 mm, the optical spectrum is acquired while emitting the UV light to acquire the optical spectrum of the fluorescence while emitting the UV light. Then, in the measurement No. 2, the emission of the UV light is stopped after a period of 500 μs has elapsed from a time point when the banknote position reaches 10 mm, and during a period of 500 μs after the emission is stopped, the optical spectrum of the phosphorescence is acquired with a gain of 2. In other words, during a period of 500 μs between the banknote positions 11 mm and 12 mm, after the light sources 603*a* and 603*b* are turned off when the banknote position reaches 11 mm, the optical spectrum of the phosphorescence is acquired with a gain of 2.

The fluorescence appears from the moment the emission of a light is started from a light source and the fluorescence disappears at the moment the emission of light from the light source is stopped. On the other hand, in the case of the phosphorescence, an afterglow phenomenon is observed in which the emission of light continues even after stopping the emission of light from the light source and the emission of light gradually disappears. Therefore, the optical spectrum of the fluorescence is acquired while the UV light is being emitted, and the optical spectrum of the phosphorescence is acquired after the emission of the UV light is stopped. The emission intensity of the phosphorescence is weaker than the emission intensity of the fluorescence. Therefore, while a gain of 1 is set in the sensor unit 34 when measuring the fluorescence in the measurement No. 1, a gain of 2 is set in the sensor unit 34 when measuring the phosphorescence in the measurement No. 2. That is, the optical spectrum of the phosphorescence is measured in the state in which the peak level of the optical spectrum of the phosphorescence has been increased. Moreover, although not included in the example shown in FIGS. 12A to 12C, as necessary, the emission quantity of the phosphorescence is increased by changing the current value of the light source units 31*a* and 31*b* set in the optical spectrum measurement condition 81. By increasing the emission quantity of the light emitted from the light sources 601*a* to 608*a* and 601*b* to 608*b*, the emission quantity of the phosphorescence is increased.

In the recognition unit 1, an optical spectrum having an appropriate peak level of the fluorescence, and an optical spectrum having an appropriate peak level of the phosphorescence can be obtained by adjusting one or more of a current value for controlling the emission quantity of the light to be emitted from the light source to excite the emission of light, a duration for which the light is to be emitted, a gain of the signal obtained by measuring the excited emission of light, and a duration for which the signal is measured. The current value and the emission duration at the time of turning on the light source and the gain and the measurement duration at the time of acquiring the signal in the sensor are set so that the features, such as peaks, clearly appear in the signal waveforms of each of the optical spectrums and the light receiving element that receives the light in the sensor unit 34 is not saturated.

In this way, after completion of the measurement of the fluorescence in the block 710 and the measurement of the fluorescence and the phosphorescence in the block 711 between the banknote positions 9 mm and 12 mm, no light source is turned on and no optical spectrum is acquired until the banknote position reaches 19 mm. Then, when the banknote 100 reaches the banknote position 19 mm, the measurement of the optical spectrum is started again.

As shown in FIGS. 12B and 12C, the measurement shown in No. 3 of the optical spectrum measurement condition 81 is performed, and the optical spectrum is acquired for the block 720 corresponding to the partial area 123. Specifically, in the measurement of No. 3, the timing at which the banknote 100 reaches the banknote position 19 mm is set to 0 μs, and during a period of 500 μs from this timing, the light sources 604*a* and 604*b* of the channel 4 of the second light source unit 31*b* are turned on at a current value of 10 mA and the IR light is emitted. Then, the measurement by the sensor unit 34 is not performed during the period of 500 μs during which the IR light is emitted. When the period of 500 μs has elapsed after the banknote position has reached 19 mm, the emission of the IR light is stopped and thereafter, the measurement by the sensor unit 34 is performed with a gain of 2 during a period of 500 μs (between the banknote positions 20 mm and 21 mm). As a result, the optical spectrum of the phosphorescence excited by the IR light in the block 720 corresponding to the partial area 123 is acquired.

After acquiring the optical spectrum of the phosphorescence in the block 720, no light source is turned on and no optical spectrum is acquired until the banknote position reaches 29 mm. Then, when the banknote 100 arrives the banknote position 29 mm, the measurement of the optical spectrum is started again.

As shown in FIGS. 12B and 12C, the measurement shown in No. 4 of the optical spectrum measurement condition 81 is performed, and the optical spectrum is acquired for the block 730 corresponding to the partial area 124. Specifically, in the measurement of No. 4, the timing at which the banknote 100 reaches the banknote position 29 mm is set to 0 μs, and during a period of 400 μs from this timing, the light sources 606*a* and 606*b* of the channel 6 of the first light source unit 31*a* and the second light source unit 31*b* are turned on at a current value of 10 mA and the UV light and the IR light are emitted. Then, the measurement by the sensor unit 34 is not performed during the period of 400 μs during which the UV light and the IR light are emitted. When the period of 400 μs has elapsed after the banknote position has reached 29 mm, the emission of the UV light and the IR light are stopped and thereafter, the measurement by the sensor unit 34 is performed with a gain of 2 during a period of 500 μs. That is, the timing at which the banknote 100 reaches the banknote position 29 mm is set to 0 (zero), and during the period of 0 μs to 400 μs, the UV light and the IR light are emitted without acquiring the optical spectrum. When 400 μs have elapsed and the emission of the UV light and the IR light is stopped, the phosphorescence excited by the UV light and the phosphorescence excited by the IR light are measured during the period of 400 μs and 900 μs.

In this manner, the measurement load can be reduced by acquiring the optical spectrum only from a predetermined partial area. In the example shown in FIGS. 12A to 12C, by measuring the optical spectrums in only four blocks among the 40 blocks 701 to 740 that constitute the banknote 100, the optical spectrums can be acquired in all the partial areas 121 to 124 in which the emission of light is observed on the banknote 100.

In this way, in the block 710 corresponding to the partial area 121, the optical spectrum shown in FIG. 11B is acquired from the fluorescence excited by the emission of the UV light. Moreover, in the block 711, the optical spectrums shown in FIG. 11C are acquired from the fluorescence and the phosphorescence excited by the emission of the UV light. Furthermore, in the block 720, the optical spectrum shown in FIG. 11D is acquired from the phosphorescence excited by the emission of the IR light. And, in the block 730, the optical spectrum shown in FIG. 11E is acquired from the phosphorescence excited by the emission of the UV light and from the phosphorescence excited by the emission of the IR light.

Figure 13A:
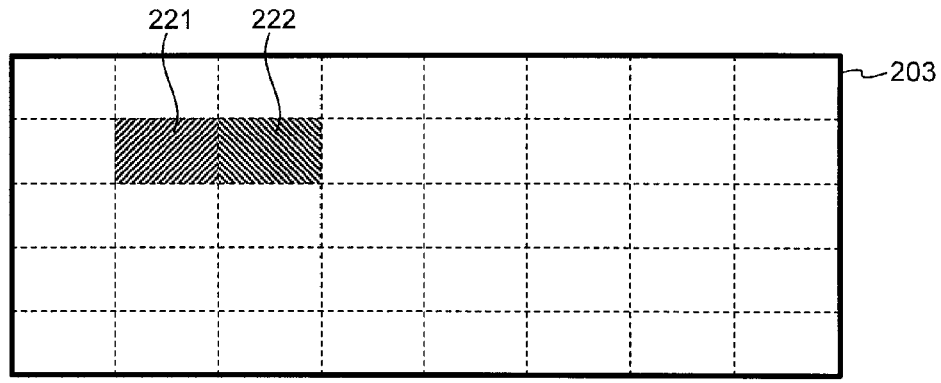
FIGS. 13A, 13B, and 13C are schematic diagrams of banknote images of the banknote shown in FIG. 11A generated based on optical spectrums.
Figure 13B:
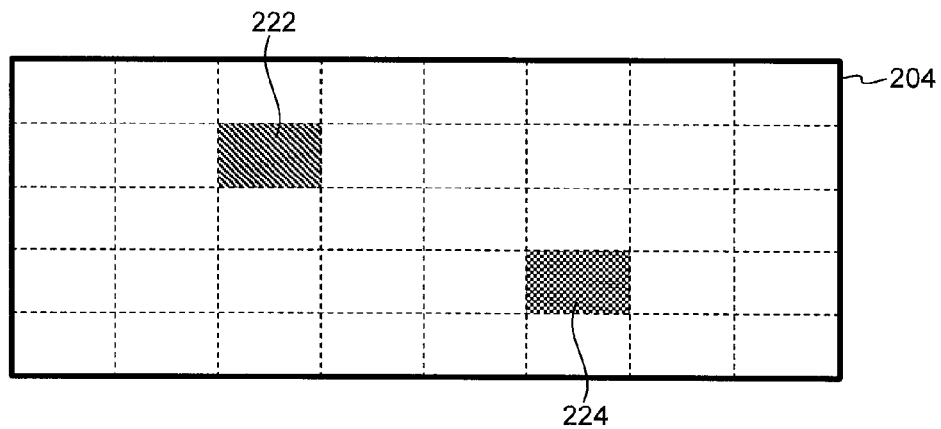
Figure 13C:
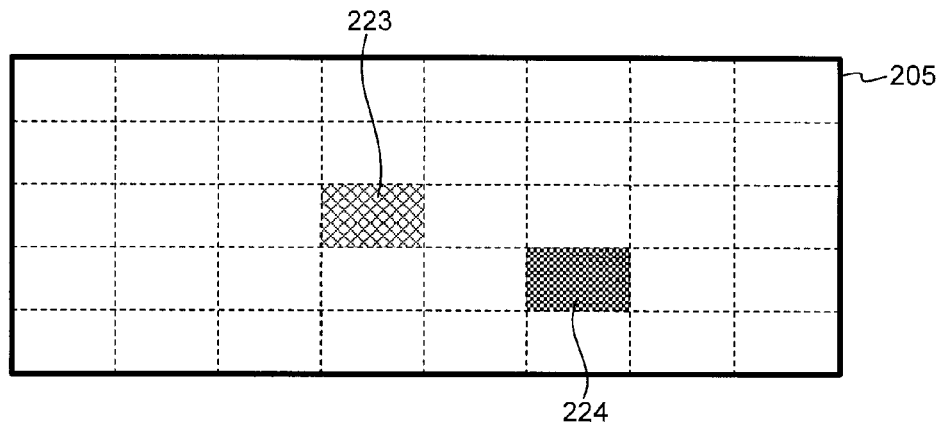

FIGS. 13A to 13C are schematic diagrams of banknote images 203 to 205 generated from the optical spectrums acquired from the partial areas 121 to 124. In the same manner as in FIGS. 7E, 10A, and 10B, in the actual banknote images 203 to 205, each of areas 221 to 224 are colored images depending on the optical spectrums; however, in FIGS. 13A to 13C these images are shown schematically with different patterns.

FIG. 13A shows the banknote image 203 generated from the optical spectrum of the fluorescence that is obtained by emitting the UV light, FIG. 13B shows the banknote image 204 generated from the optical spectrum of the phosphorescence that is obtained by emitting the UV light, and FIG. 13C shows the banknote image 205 generated from the optical spectrum of the phosphorescence that is obtained by emitting the IR light. In this manner, in the recognition unit 1, various banknote images 203 to 205 can be generated depending on the type of the light emitted from the light source unit 31 and the type of the excited light.

As shown in FIGS. 11A to 11E, because the optical spectrum of the fluorescence is acquired in the partial areas 121 and 122 by emission of the UV light, as shown in FIG. 13A, the partial areas 221 and 222 on the banknote image 203 corresponding to the partial areas 121 and 122 on the banknote 100 are images of colors that depend on the optical spectrums. Moreover, because the optical spectrum of the phosphorescence is acquired in the partial areas 122 and 124 by emission of the UV light, as shown in FIG. 13B, the partial areas 222 and 224 on the banknote image 204 corresponding to the partial areas 122 and 124 on the banknote 100 are images of colors that depend on the optical spectrums. Furthermore, because the optical spectrum of the phosphorescence is acquired in the partial areas 123 and 124 by emission of the IR light, as shown in FIG. 13C, the partial areas 223 and 224 on the banknote image 205 corresponding to the partial areas 123 and 124 on the banknote 100 are images of colors that depend on the optical spectrums.

In FIGS. 11A to 13C, explanation has been given about a case of acquiring the optical spectrums of the visible fluorescence and the visible phosphorescence by emitting the UV light and acquiring the optical spectrums of the IR fluorescence and the IR phosphorescence by emitting the IR light; however, the present embodiment is not limited to this configuration. Specifically, for example, it is allowable to acquire optical spectrums of the IR fluorescence and the IR phosphorescence when the UV light is emitted and to acquire the IR fluorescence and the IR phosphorescence when the visible light is emitted. The wavelength band of the light emitted on the banknote 100 and the wavelength band of the optical spectrum to be acquired from the banknote 100 can be determined appropriately depending on the luminous phenomenon to be excited on the banknote 100.

If the banknote image of the fluorescence acquired when the UV light is emitted, the banknote image of the phosphorescence acquired when the UV light is emitted, and the banknote image of the phosphorescence acquired when the IR light is emitted on the banknote 100 shown in FIG. 11A are previously stored in the memory 80 as the data for recognition 82, it can be determined whether the banknote 100 that is being transported is the banknote 100 shown in FIG. 11A or not, based on a correlation between these previously stored images and the banknote images 203 to 205 that are generated from the optical spectrums acquired from the banknote 100 that is being transported on the transport path 60.

In the above examples, a case has been explained in which the light source of the channel is turned on at the timing when the area in which the emission is observed passes right below the light source; however, the present embodiment is not limited to this configuration. The configuration can be changed to a configuration in which the light source emits the light from an inclined direction on the emission area by setting the optical spectrum measurement condition 81. The optical spectrum measurement condition 81 can be set so that the light is emitted from an inclined direction on the emission area by changing the above explained configuration or by preparing a new configuration in addition to the above explained configuration. Moreover, in the measurement of the phosphorescence, the timing at which the emission of light is started in the emission area, the timing to stop the emission of light, and the timing to start the measurement of the phosphorescence can be set to different values from those mentioned in the above examples. For example, the acquisition of the optical spectrum from all the blocks of the banknote 100 that is transported at 2000 mm/s can be performed during a period of 500 µs, and it is allowable to perform a setting so that, when measuring the fluorescence, the emission of light and the measurement of the fluorescence from a light source is performed during this period of 500 µs, and when measuring the phosphorescence, the emission of light from the light source, stopping of the emission of light, and the measurement of the phosphorescence are all completed during this period of 500 µs. Specifically, for example, it is allowable to set to emit the light from a light source during a period of 0 µs and 400 µs in one block, stop the emission of the light from the light source, and perform the measurement of the phosphorescence during a period of 400 µs and 500 µs. There are situations in which, for example, it is necessary to measure the fluorescence or the phosphorescence in the next block right after measuring the phosphorescence in the current block. By adopting the above setting, even in the above situations, after acquiring the optical spectrum relating to the phosphorescence during a period of 500 µs in the current block, it is possible to acquire the optical spectrum of the fluorescence or the phosphorescence successively in the next block during a period of 500 µs.

In this manner, in the recognition unit 1, it is possible to select one or more of the light sources that shall be turned on to excite the emission of light in each of the partial areas on the banknote 100 by setting appropriate optical spectrum measurement condition 81. Moreover, in the optical spectrum measurement condition 81, depending on the type, the wavelength band, the emission quantity, and the like, of the light excited in each of the partial areas, it is possible to set the type (wavelength), the emission quantity, the emission angle, the start timing and the stop timing of the emission of the light from the selected light source, the start timing and the stop timing of the measurement of the light excited in each of the partial areas, the gain of the measurement, and the like. Accordingly, it is possible to excite the light in a desired partial area on the banknote 100 that is transported at a high speed on the transport path 60 and acquire the optical spectrum of the excited light.

Moreover, in the recognition unit 1, apart from using the feature in the optical spectrums, such as the peak wavelength, the peak level, and the like, appearing in the optical spectrum, and the banknote image generated from the optical spectrum in the recognition of the banknote 100, it is possible to perform the recognition of the denomination and the like of the banknote 100 based on the signal waveform of the optical spectrum. Specifically, for example, if the signal waveform of the optical spectrum obtained per denomination of the banknote 100 are previously stored in the memory 80 as the data for recognition 82, the recognition processing unit 74 can recognize the denomination and the like of the banknote 100 based on a correlation between the signal waveform of the optical spectrum obtained by the data acquisition unit 73 and the signal waveform stored as the data for recognition 82.

In the recognition unit 1, the process by the spectroscopy unit 30 can be performed after finishing the process by the recognition sensor unit 20. Alternatively, the process by the recognition sensor unit 20 and the process by the spectroscopy unit 30 can be performed in parallel.

Figure 14:
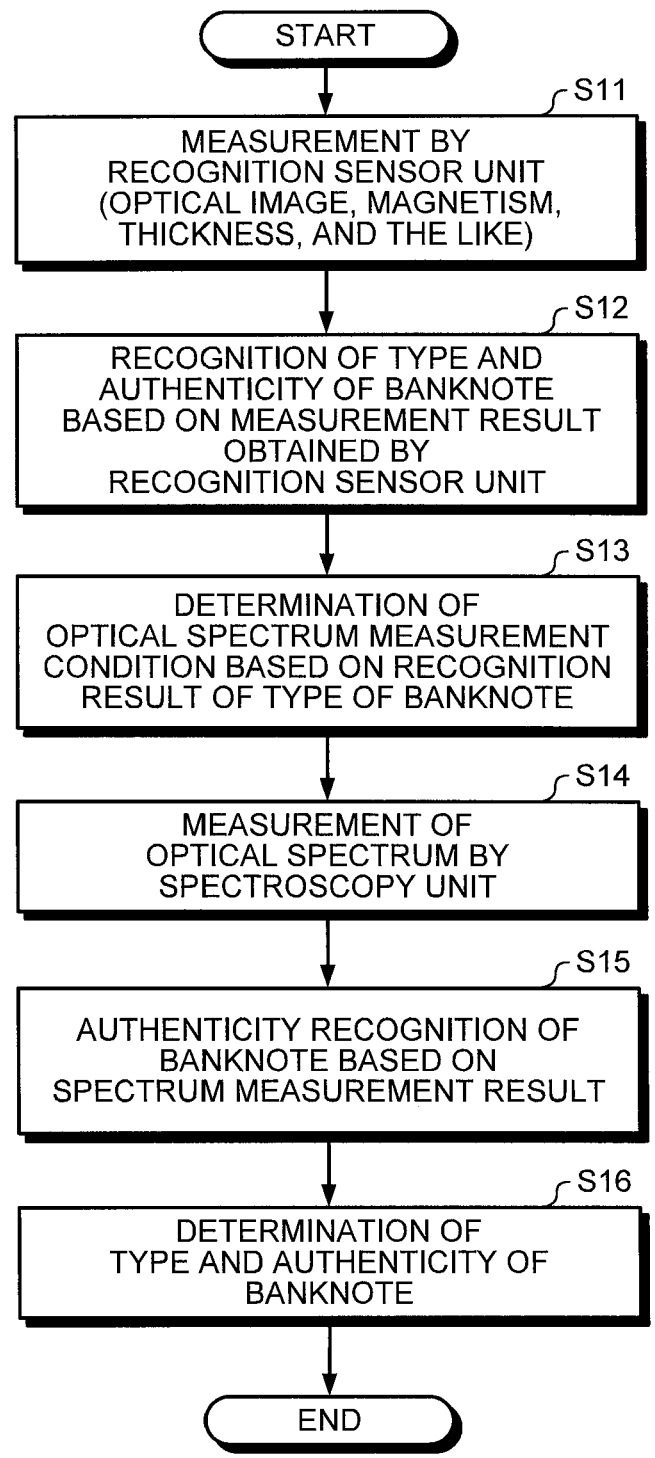
FIG. 14 is a flowchart indicating a situation in which a process by a recognition sensor unit and a process by the spectroscopy unit are performed serially.

FIG. 14 is a flowchart indicating a situation in which the process by the recognition sensor unit 20 and the process by the spectroscopy unit 30 are performed serially. At first, the recognition sensor unit 20 performs measurement of an image, magnetic characteristic, a thickness, and the like of the banknote 100 (Step S11), and a type and authenticity of the banknote 100 are recognized based on the result of measurement (Step S12). Subsequently, the optical spectrum measurement condition 81 suitable for the recognized type of the banknote 100 is read from the memory 80 (Step S13). Then, the spectroscopy unit 30 performs the measurement of the optical spectrum by using the read optical spectrum measurement condition 81 (Step S14). Once the result of the measurement of the optical spectrum is obtained, the authenticity of the banknote 100 is recognized based on a comparison with the data for recognition 82 stored in the memory 80 (Step S15). In this way, once the recognition results of the type and the authenticity of the banknote 100 are obtained by the recognition sensor unit 20, and the recognition result of the authenticity of the banknote 100 is obtained by the spectroscopy unit 30, the type and the authenticity of the banknote 100 are finally determined based on these results (Step S16).

FIG. 15 is a flowchart indicating a situation in which the process by the recognition sensor unit 20 and the process by the spectroscopy unit 30 are performed in parallel. At first, the recognition sensor unit 20 performs measurement of an image, magnetic characteristic, a thickness, and the like of the banknote 100 (Step S21), and a type and authenticity of the banknote 100 are recognized based on the result of measurement (Step S23). In parallel to these processes (Steps S21 and S23), the spectroscopy unit 30 measures the optical spectrum (Step S22), and the type and the authenticity of the banknote 100 are recognized based on the result of measurement (Step S24).

When performing the measurement by the spectroscopy unit 30 in a state in which the type of the banknote 100 is not known, the measurement of the optical spectrum necessary to distinguish all the types of the banknote 100 from each other is performed. For example, when the banknote 100 handled by the banknote handling apparatus 2 is of a predetermined country, the partial areas in the banknote 100, the light source corresponding to each of the partial areas, the wavelength of light emitted from the light source, the timing and the duration of the emission, the timing and the duration of the measurement of the optical spectrum, and the like, that need to be measured to recognize the type of the banknote 100 of this country are previously stored in the memory 80 as the optical spectrum measurement condition 81. By performing the measurement based on this optical spectrum measurement condition 81, depending on the type of the banknote 100, a predetermined optical spectrum can be acquired from a predetermined partial area. For example, by previously preparing the information, such as the optical spectrum to be obtained from the banknote and the partial area from which this optical spectrum is to be obtained, as the data for recognition 82 per type of the banknote 100, the type and the authenticity of the banknote 100 can be recognized based on the data for recognition 82 and the optical spectrum obtained from the banknote 100 that is transported on the transport path 60. Similarly, by previously preparing the banknote image obtained from the optical spectrum as the data for recognition 82 per type of the banknote 100, the type and the authenticity of the banknote 100 can be recognized based on the data for recognition 82 and the banknote image obtained from the optical spectrum of the banknote 100 that is transported on the transport path 60.

In this way, once the recognition results of the type and the authenticity of the banknote 100 are obtained by the recognition sensor unit 20, and the recognition result of the authenticity of the banknote 100 is obtained by the spectroscopy unit 30, the type and the authenticity of the banknote 100 are determined based on these results (Step S25).

Apart from performing the recognition of the type, such as the denomination or the year of issuance, and the like, of the banknote 100, and the recognition of the authenticity of the banknote 100, by using the measurement made by the spectroscopy unit 30, it is possible to determine the fitness of the banknote 100. The optical spectrums having the same waveforms are typically obtained from the banknotes 100 of the same type; however, a waveform of the optical spectrum of the banknote 100 changes in a predetermined frequency depending on the level of damage of the banknote 100. By using this fact, the fitness of the banknote 100 can be determined in the recognition unit 1 based on the waveform of the optical spectrum of a predetermined wavelength band.

In the present embodiment, an example of emitting the ultraviolet light and the infrared light from the light source unit 31 has been explained; however, the type of the light to be emitted is not limited to the ultraviolet light and the infrared light. For example, when it is possible to recognize the banknote 100 by using only the ultraviolet light or only the infrared light, it is allowable to emit only one type of light from the light source unit 31. Moreover, it is allowable to use as the light emitted from the light source unit 31 three or more type of lights including a white light, a visible light of a predetermined wavelength, and the like, in addition to the ultraviolet light and the infrared light.

Moreover, the number of the light receiving surfaces of the reading unit 32 is not limited to 16, and the number of the channels is also not limited to 8 channels. The number of light receiving surfaces, the number of channels, the number of light sources, the type of the light to be emitted from the light source, and the like, can be suitably determined depending on the luminous phenomenon observed of the banknote 100 that is the target of recognition and the position and the size of the partial area in which the light is excited.

Moreover, in the measurement No. 1 shown in FIG. 12B, the measurement by the sensor unit 34 is performed multiple times. Similarly, the radiation of the light from the light sources 601a to 608a and 601b to 608b can be performed multiple times. Specifically, for example, when the fluorescence and the phosphorescence are excited by the light emitted from the same light source, it is allowable to first turn on the light source at a current value set for exciting the fluorescence, and then turn on the same light source at a current value set for exciting the phosphorescence. By using the optical spectrum measurement condition 81, during one measurement, the timing, the duration, and the number of times to emit the light from the light source, and the timing, the duration, and the number of times to measure the excited light can be set depending on the light to be used as the measurement target.

Moreover, in the present embodiment, in one measurement, only the light source corresponding to one block is turned on and the optical spectrum in this block is acquired; however, the configuration is not limited to this configuration. Specifically, a light source of each of a plurality of channels can be turned on simultaneously and an optical spectrum of a block corresponding to each of the channels can be acquired simultaneously. For example, if the optical spectrums of different wavelength bands are obtained in the block 701 and the block 705 shown in FIG. 6A, the light sources 601a and 601b of the channel 1 corresponding to the block 701 and the light sources 605a and 605b of the channel 5 corresponding to the block 705 can be turned on simultaneously to acquire the optical spectrums from the block 701 and the block 705 simultaneously. If the light is excited in a plurality of partial areas on the banknote 100 in the main scanning direction of the reading unit 32, and these emitted lights show the optical spectrums of different wavelength bands, then it is allowable to set a block suitable for each of the partial areas, simultaneously turn on the light source corresponding to each block, and set the optical spectrum measurement condition 81 that allows the optical spectrums to be measured simultaneously.

As mentioned above, according to the present embodiment, by controlling the turning on/off of the plurality of the light sources 601a to 608a and 601b to 608b that are arranged so as to emit the lights in the plurality of partial areas on the banknote 100 based on the optical spectrum measurement condition 81, and by controlling the timing of acquiring the optical spectrum by the sensor unit 34, the optical spectrums of the fluorescence and the phosphorescence can be acquired. Moreover, the type, the authenticity, the fitness, and the like, of the banknote 100 can be recognized by using the obtained optical spectrum or the banknote image generated by using the optical spectrum.

INDUSTRIAL APPLICABILITY

As explained above, the paper sheet recognition apparatus and the paper sheet recognition method according to the present invention are used in recognizing a paper sheet based on the data relating to the optical characteristics acquired efficiently from a plurality of areas on the paper sheet.

EXPLANATION OF REFERENCE NUMERALS

1 recognition unit (paper sheet recognition apparatus)
2 banknote handling apparatus
10 money inlet
20 recognition sensor unit
30 spectroscopy unit
31, 31a, 31b light source unit
32 reading unit
33 light guide unit
34 sensor unit
40 storing unit
50 reject outlet
60 transport path
61 upper guide
62 lower guide
70 control unit
71 transport information acquisition unit
72 light-source control unit
73 data acquisition unit
74 recognition processing unit
80 memory
81 optical spectrum measurement condition
82 data for recognition
90 display unit
311 transparent member
312 casing
322 base member
401 to 404 light guiding plate
501 to 516 light receiving surface
601a to 608a, 601b to 608b light source

The invention claimed is:

1. A paper sheet recognition apparatus that recognizes a paper sheet by using an optical spectrum acquired by emitting light on the paper sheet transported on a transport path, the paper sheet recognition apparatus comprising:
a light source unit including a plurality of light sources arranged corresponding to a plurality of partial areas on the paper sheet;
a reading unit having a light receiving surface that is arranged so as to receive reflected light from the plurality of partial areas;
a sensor unit that acquires an optical spectrum of the light received by the reading unit;
a memory that stores therein an optical spectrum measurement condition including a plurality of pieces of information associated with each other for acquiring the optical spectrum of light received from a predetermined partial area on the paper sheet, the plurality of pieces of information including information for identifying at least one light source corresponding to the predetermined partial area among the plurality of light sources of the light source unit, information for identifying a timing for turning on the at least one light source, and information for identifying a timing for turning off the at least one light source that is turned on at the timing for turning on; and
a light-source control unit that controls the light source unit based on the optical spectrum measurement condition
wherein the light source unit emits the light to any target partial area out of the plurality of partial areas, and the sensor unit acquires the optical spectrum of the light received from the target partial area.

2. The paper sheet recognition apparatus as claimed in claim 1, wherein the plurality of pieces of information associated with each other in the optical spectrum measurement condition further includes information for identifying an emission quantity of the light emitted from the at least one light source while the at least one light source is turned on.

3. The paper sheet recognition apparatus as claimed in claim 1, wherein the plurality of pieces of information associated with each other in the optical spectrum measurement condition further includes information for identifying a timing to start an acquisition of the optical spectrum by the sensor unit, and information for identifying a timing to stop the acquisition of the optical spectrum.

4. The paper sheet recognition apparatus as claimed in claim 1, wherein the plurality of pieces of information associated with each other in the optical spectrum measurement condition further includes information for identifying an adjustment amount of a signal gain for acquiring the optical spectrum by the sensor unit.

5. The paper sheet recognition apparatus as claimed in claim 1, wherein
the optical spectrum measurement condition is prepared for each type and each orientation of the paper sheet in the memory, and
the light-source control unit reads from the memory the optical spectrum measurement condition corresponding to a type and an orientation of the paper sheet that is being transported on the transport path and controls the light source unit based on a read optical spectrum measurement condition.

6. The paper sheet recognition apparatus as claimed in claim 1, wherein
the light source unit is capable of emitting at least two types of light having different wavelength bands, and
the information for identifying the light source in the optical spectrum measurement condition includes information to identify a type of the light.

7. The paper sheet recognition apparatus as claimed in claim 1, wherein
the light source unit includes
one light source that emits light from an upstream side in a transport direction to a light receiving area on the paper sheet; and
another light source that emits light from a downstream side in the transport direction to the light receiving area.

8. The paper sheet recognition apparatus as claimed in claim 1, wherein an image of the target partial area is generated based on the optical spectrum acquired from the partial area by the sensor unit, and a paper sheet image indicating optical characteristics of the paper sheet is generated from the image of the target partial area.

9. The paper sheet recognition apparatus as claimed in claim 1, further comprising
a light guide unit that guides the light received by the reading unit to the sensor unit.

10. A paper sheet recognition method for recognizing a paper sheet by using an optical spectrum acquired from the paper sheet transported on a transport path, the paper sheet recognition method comprising:
acquiring an optical spectrum measurement condition that includes a plurality of pieces of information associated with each other, the plurality of pieces of information including information for identifying at least one light source, which corresponds to any target partial area out of a plurality of partial areas on the paper sheet, among a plurality of light sources included in a light source unit, information for identifying a timing for turning on the at least one light source, and information for identifying a timing for turning off the at least one light source that is turned on at the timing for turning on;
controlling the light source unit based on the optical spectrum measurement condition to emit light to the target partial area;
receiving light from the target partial area by a reading unit that is arranged so as to receive light from the plurality of partial areas; and
acquiring an optical spectrum of the light received from the target partial area by a sensor unit.

\* \* \* \* \*